United States Patent [19]

Wu

[11] Patent Number: 6,150,513
[45] Date of Patent: Nov. 21, 2000

[54] POLYKETIDE SYNTHASE ENZYMES AND RECOMBINANT DNA CONSTRUCTS THEREFOR

[75] Inventor: Kai Wu, Foster City, Calif.

[73] Assignee: Kosan Biosciences, Inc., Hayward, Calif.

[21] Appl. No.: 09/154,083

[22] Filed: Sep. 16, 1998

[51] Int. Cl.[7] .......................... C12N 15/52; C12N 15/31; C12N 15/63; C12N 15/70; C12N 15/74

[52] U.S. Cl. .................... 536/23.2; 536/23.7; 435/183; 435/189; 435/252.3; 435/320.1

[58] Field of Search .................... 435/189, 183, 435/252.3, 320.1; 536/23.2

[56] References Cited

U.S. PATENT DOCUMENTS

| | | |
|---|---|---|
| 4,874,748 | 10/1989 | Katz et al. . |
| 5,063,155 | 11/1991 | Cox et al. . |
| 5,098,837 | 3/1992 | Beckmann et al. . |
| 5,116,756 | 5/1992 | Dumont et al. . |
| 5,149,639 | 9/1992 | Katz et al. . |
| 5,672,491 | 9/1997 | Khosla et al. . |
| 5,712,146 | 1/1998 | Khosla et al. . |
| 5,712,496 | 1/1998 | Takahashi et al. .................. 257/64 |
| 5,824,513 | 10/1998 | Donadio et al. .................. 435/79 |
| 5,876,991 | 3/1999 | DeHoff et al. .................. 435/183 |

FOREIGN PATENT DOCUMENTS

| | | |
|---|---|---|
| WO 93/13663 | 7/1993 | WIPO . |
| WO 95/08548 | 3/1995 | WIPO . |
| WO 96/40968 | 12/1996 | WIPO . |
| WO 97/02358 | 1/1997 | WIPO . |
| WO 98/27203 | 6/1998 | WIPO . |

OTHER PUBLICATIONS

Caffrey et al, *FEBS Letters* 304:205 (1992).
Fu et al, *Biochemistry* 33:9321–9326 (1994).
McDaniel et al., *Science* 262:1546–1550 (1993).
Motamedi et al., "Structural organization of a multifunctional polyketide synthase involved in the biosynthesis of the macrolide immunosuppressant FK506", *Eur. J. Biochem.*, 244, pp. 74–80, (1997).
Rohr, *Angew. Chem. Int. Ed. Engl.* 34(8):881–888 (1995).
Schwecke et al., "The biosynthetic gene cluster for the polyketide immunosuppressant rapamycin", *Proc. Nat'l Acad. Sci. USA* 92 (Aug. 1995), pp. 7839–7843.

*Primary Examiner*—Ponnathapu Achutamurthy
*Assistant Examiner*—William W. Moore
*Attorney, Agent, or Firm*—Morrison & Foerster, LLP; Kevin Kaster

[57] ABSTRACT

Host cells comprising recombinant vectors encoding the FK-520 polyketide synthase and FK-520 modification enzymes can be used to produce the neuroimmunophilin FK-520 polyketide. Recombinant DNA constructs comprising one or more FK-520 polyketide synthase domains, modules, open reading frames, and variants thereof can be used to produce recombinant polyketide synthases and a variety of different polyketides with application in agriculture, medicine, and animal health.

5 Claims, 1 Drawing Sheet

SEQUENCE LISTING

<160> NUMBER OF SEQ ID NOS: 31

<210> SEQ ID NO 1
<211> LENGTH: 748
<212> TYPE: DNA
<213> ORGANISM: Streptomyces hygroscopicus

<400> SEQUENCE: 1
gaagaactcc gcgtcgaagt ctccggcgcc gttcacgaag ccgccctcgc ggacgtacga      60
ggtaccgggg tggtcggggt ccgggtggta cagggcgtcc atgtcccagc cccggtcggt     120
ggggaacgcg gtcatcccgt cacggccctc ggccaccagc cgccacaggt cttcgggcga     180
ctccacatcg cccgggaggc ggcaggccat cgccacgatc gcgatggggt catcatcggc     240
gacggccacc gccgtggcct cggtgacgtc ctccgcaccg agcaactcgg cgcgcaggtg     300
ctgggccagc gcgttcggcg agggtggtc gaagacgagg gtggcgggca gccgcagccc     360
ggtggcggcg ttcagccggt tgcggagttc cacggccgtg agcgagtcga agccagctcc     420
ttgaacgcct tcgtcgcgtt cacggcttcc tgcgaggtgt gccgagcacg gcggcacgtc     480
ggcgcgtaca ggtccagcag gatgcgcggc tcgctcggac gcggcggcag cggcgtgcag     540
cgcgagcccg gcgccgtgcg tacgacgcgc gacgcgcgga cgtggcgtac agccctgaac     600
gcgcggagcc accgtctgcg acgccggcag tcagtgaggg accgaccgtg ttcggcagcc     660
gctgacggtc aacgtcatca atgcatgtgg acatcgccgc tatcggcgat tcgcttcaag     720
tcggatcagt actcgtcagg cagaagag                                       748

<210> SEQ ID NO 2
<211> LENGTH: 249
<212> TYPE: PRT
<213> ORGANISM: Streptomyces hygroscopicus

<400> SEQUENCE: 2

Glu Glu Leu Arg Val Glu Val Ser Gly Ala Val His Glu Ala Ala Leu
 1               5                  10                  15

Ala Asp Val Arg Gly Thr Gly Val Val Gly Val Arg Val Val Gln Gly
             20                  25                  30

Val His Val Pro Ala Pro Val Gly Gly Glu Arg Gly His Pro Val Thr

```
                  35                  40                  45
Ala Leu Gly His Gln Pro Pro Gln Val Phe Gly Arg Leu His Ile Ala
            50                  55                  60
Arg Glu Ala Ala Gly His Arg His Asp Arg Asp Gly Val Ile Ile Gly
 65                  70                  75                  80
Asp Gly His Arg Arg Gly Leu Gly Asp Val Leu Arg Thr Glu Gln Leu
                85                  90                  95
Gly Ala Gln Val Leu Gly Gln Arg Val Arg Gly Val Val Glu Asp
            100                 105                 110
Glu Gly Gly Gln Pro Gln Gly Gly Val Gln Pro Val Ala
        115                 120                 125
Glu Phe His Gly Arg Glu Arg Val Glu Ala Ser Ser Leu Asn Ala Phe
        130                 135                 140
Val Ala Phe Thr Ala Ser Cys Glu Val Cys Arg Ala Arg His Val
145                 150                 155                 160
Gly Ala Tyr Arg Ser Ser Arg Met Arg Gly Ser Leu Gly Arg Gly Gly
                165                 170                 175
Ser Gly Val Gln Arg Glu Pro Gly Ala Val Arg Thr Thr Arg Asp Ala
            180                 185                 190
Arg Thr Trp Arg Thr Ala Leu Asn Ala Arg Ser His Arg Leu Arg Arg
        195                 200                 205
Arg Gln Ser Val Arg Asp Arg Pro Cys Ser Ala Ala Asp Gly Gln
    210                 215                 220
Arg His Gln Cys Met Trp Thr Ser Pro Leu Ser Ala Ile Arg Phe Lys
225                 230                 235                 240
Ser Asp Gln Tyr Ser Ser Gly Arg Arg
                245

<210> SEQ ID NO 3
<211> LENGTH: 640
<212> TYPE: DNA
<213> ORGANISM: Streptomyces hygroscopicus

<400> SEQUENCE: 3
ggcgggcgcc gtggccgacc gggactctcc accgaacacg tcgacgccgt ggacgcccat    60
ggaacgggga ccccgctcgg tgacccatc gaggcccagg cgctgctggc cacctacggc   120
cgggaccggg cggcggaccg gcccctgtgt ctgggctcgc tgaagtcgaa catcgggcat   180
acgcaggcgg cggccggtgt cggcggtgtc atcaagatgt tgatgcgat gcggcacggt   240
gtgctgccga agacgttgca tgtggaggag ccgacgccgc atgtggactg gtcgtcgggt   300
gcggtctcgc tgctgacgga ggcgcgggag tggccggaga cggacggccg gccgcgccgg   360
gcggccgtgt cgtccttcgg catcagcggc accaacgccc acgtcatcct cgaacagccg   420
ccggctccgg ccgacgaaca gccgatggtg agccgggtcc cggcccagcc accgcgctgc   480
ctgggtgatc tccggcggga gtgccgatgc ctgcgcgaac aggccgccgg ctggcgtcgt   540
cctcgacgag gtggagtgcg agagacggac ctgaagaggc ggacggcacc ggcatcgtgc   600
gcgtcacccc gctgacctcg cgtattcgct cgccaacttt                          640

<210> SEQ ID NO 4
<211> LENGTH: 212
<212> TYPE: PRT
<213> ORGANISM: Streptomyces hygroscopicus

<400> SEQUENCE: 4
```

-continued

```
Gly Gly Arg Arg Gly Arg Pro Gly Leu Ser Thr Glu His Val Asp Ala
 1               5                  10                  15
Val Asp Ala His Gly Thr Gly Thr Pro Leu Gly Asp Pro Ile Glu Ala
             20                  25                  30
Gln Ala Leu Leu Ala Thr Tyr Gly Arg Asp Arg Ala Ala Asp Arg Pro
             35                  40                  45
Leu Trp Leu Gly Ser Leu Lys Ser Asn Ile Gly His Thr Gln Ala Ala
         50                  55                  60
Ala Gly Val Gly Gly Val Ile Lys Met Val Met Ala Met Arg His Gly
 65              70                  75                  80
Val Leu Pro Lys Thr Leu His Val Glu Glu Pro Thr Pro His Val Asp
                 85                  90                  95
Trp Ser Ser Gly Ala Val Ser Leu Leu Thr Glu Ala Arg Glu Trp Pro
                100                 105                 110
Glu Thr Asp Gly Arg Pro Arg Arg Ala Ala Val Ser Ser Phe Gly Ile
                115                 120                 125
Ser Gly Thr Asn Ala His Val Ile Leu Glu Gln Pro Pro Ala Pro Ala
        130                 135                 140
Asp Glu Gln Pro Met Val Ser Arg Val Pro Ala Gln Pro Pro Arg Cys
145                 150                 155                 160
Leu Gly Asp Leu Arg Arg Glu Cys Arg Cys Leu Arg Glu Gln Ala Ala
                165                 170                 175
Gly Trp Arg Arg Pro Arg Arg Gly Val Arg Glu Thr Asp Leu Lys
                180                 185                 190
Arg Arg Thr Ala Pro Ala Ser Cys Ala Ser Pro Arg Pro Arg Val Phe
                195                 200                 205
Ala Arg Gln Leu
        210
```

<210> SEQ ID NO 5
<211> LENGTH: 237
<212> TYPE: DNA
<213> ORGANISM: Streptomyces hygroscopicus

<400> SEQUENCE: 5

```
ccaggccggg ttcctggacc ggcttggacc gcgttgacgc gcggggagcc gtcgcctctg    60
gttgtcgagg gcgtggcgac gacgggtccg gtggcctttc tcttcgacgg gtcacggggt   120
acgcagcggt gggatgggg gcgtgagctg tatgagtcgt atccggtgtt cgcggaggcg   180
ttcgacgcgg tgtgtgaggg gttcgcgccg ctgccggtga aggacgtggt gttcggg    237
```

<210> SEQ ID NO 6
<211> LENGTH: 79
<212> TYPE: PRT
<213> ORGANISM: Streptomyces hygroscopicus

<400> SEQUENCE: 6

```
Pro Gly Arg Val Pro Gly Pro Ala Trp Thr Ala Leu Thr Arg Gly Glu
 1               5                  10                  15
Pro Ser Pro Leu Val Val Glu Gly Val Ala Thr Thr Gly Pro Val Ala
             20                  25                  30
Phe Leu Phe Asp Gly Ser Arg Gly Thr Gln Arg Val Gly Met Gly Arg
             35                  40                  45
Glu Leu Tyr Glu Ser Tyr Pro Val Phe Ala Glu Ala Phe Asp Ala Val
         50                  55                  60
Cys Glu Gly Phe Ala Pro Leu Pro Val Lys Asp Val Val Phe Gly
```

```
               65                  70                  75

<210> SEQ ID NO 7
<211> LENGTH: 806
<212> TYPE: DNA
<213> ORGANISM: Streptomyces hygroscopicus

<400> SEQUENCE: 7
gatatcaccg tggcgtgcgg gccgttgacg gccgcgatgg cgacccggtc gatggcgatc      60
tggtccatgg cgacctggtc agagccggtc agcgacgcgc gcacctcggc ctcgccggcc     120
cgcaccgaca ccatcgcccc gcccggcggc agcgcctgca tcagccgccc gcgcgccgcg     180
acgagccggc aggcgtcggg gagggagagg acgccggaga catgggcggc cgcgagttcg     240
ccgaccgaat gccccagcag atagtcgggg cgcacccccc aggactccag caaccggaac     300
agcgccacct cgacggcgaa cagggcgggc tgcgcgtact cggtacggtc cagcagctcc     360
tggtcggcgc cgaacaccac gtccttcagc ggccgctcca gctccagccg ctcgcagacc     420
gcgtcgaacg cctcggcgaa caccgggtac gtcgcgtaca gctcacgccc atgccgccgc     480
gtggggcccc tgacagggaa gaggaggcgc actcgcctcc acgaccgtgc ccgtcacggt     540
gttcggttcg gctcgcccgc cgcgaggtgt tcagcgccgc ccgaaacccc tctcgttcgt     600
cgcgagagca cggcgcgctc agcccggccg aatgtgtggc agcgcacgcc gatgtcgggc     660
gggcgggtcc tcgggtggtc gtcaagttac gggcgcagcc gcttcgccgt gggcgggagg     720
gcctgttcgt cttggcgcac gaatcagggc cgcgcgttgg acgtacgtgg gctggtgggc     780
atggtcctgg gcgtttggca ggcggg                                          806

<210> SEQ ID NO 8
<211> LENGTH: 265
<212> TYPE: PRT
<213> ORGANISM: Streptomyces hygroscopicus

<400> SEQUENCE: 8

Pro Ala Cys Gln Thr Pro Arg Thr Met Pro Thr Ser Pro Arg Thr Ser
  1               5                  10                  15

Asn Ala Arg Pro Phe Val Arg Gln Asp Glu Gln Ala Leu Pro Pro Thr
                 20                  25                  30

Ala Lys Arg Leu Arg Pro Leu Asp Asp His Pro Arg Thr Arg Pro Pro
             35                  40                  45

Asp Ile Gly Val Arg Cys His Thr Phe Gly Arg Ala Glu Arg Ala Val
         50                  55                  60

Leu Ser Arg Arg Thr Arg Gly Val Ser Gly Ala Glu His Leu Ala
 65                  70                  75                  80

Ala Gly Glu Pro Asn Arg Thr Pro Arg Ala Arg Ser Trp Arg Val
                 85                  90                  95

Arg Leu Leu Phe Pro Val Arg Gly Pro Thr Arg Arg His Gly Arg Glu
                100                 105                 110

Leu Tyr Ala Thr Tyr Pro Val Phe Ala Glu Ala Phe Asp Ala Val Cys
            115                 120                 125

Glu Arg Leu Glu Leu Glu Arg Pro Leu Lys Asp Val Val Phe Gly Ala
        130                 135                 140

Asp Gln Glu Leu Leu Asp Arg Thr Glu Tyr Ala Gln Pro Ala Leu Phe
145                 150                 155                 160

Ala Val Glu Val Ala Leu Phe Arg Leu Leu Glu Ser Trp Gly Val Arg
                165                 170                 175
```

```
Pro Asp Tyr Leu Leu Gly His Ser Val Gly Glu Leu Ala Ala Ala His
                180                 185                 190

Val Ser Gly Val Leu Ser Leu Pro Asp Ala Cys Arg Leu Val Ala Ala
            195                 200                 205

Arg Gly Arg Leu Met Gln Ala Leu Pro Pro Gly Gly Ala Met Val Ser
        210                 215                 220

Val Arg Ala Gly Glu Ala Glu Val Arg Ala Ser Leu Thr Gly Ser Asp
225                 230                 235                 240

Gln Val Ala Met Asp Gln Ile Ala Ile Asp Arg Val Ala Ile Ala Ala
                245                 250                 255

Val Asn Gly Pro His Ala Thr Val Ile
                260                 265

<210> SEQ ID NO 9
<211> LENGTH: 345
<212> TYPE: DNA
<213> ORGANISM: Streptomyces hygroscopicus

<400> SEQUENCE: 9
ggcttttccc tggcgacgac gagggactcc ttcccccacc gcgccgtggt gaccgcacat     60
gaccaggccg ggttcctgga cggcttggac gcgttgacgc gcggggagcc gtcgcctctg    120
gttgtcgagg gcgtggcgac gacgggtccg gtggcctttc tcttcgcggg tcaggggtcg    180
cagcgggtgg ggatggggcg tgagctgtat gagtcgtatc cggtgttcgc ggaggcgttc    240
gacgcggtgt gtgaggggtt cgcgccgctg ccggtgaagg acgtggtgtt cggagctgac    300
caggagctgc tggatcgtac ggagttcgct cagcctgcgc tgttt                    345

<210> SEQ ID NO 10
<211> LENGTH: 115
<212> TYPE: PRT
<213> ORGANISM: Streptomyces hygroscopicus

<400> SEQUENCE: 10

Gly Phe Ser Leu Ala Thr Thr Arg Asp Ser Phe Pro His Arg Ala Val
1               5                   10                  15

Val Thr Ala His Asp Gln Ala Gly Phe Leu Asp Gly Leu Asp Ala Leu
                20                  25                  30

Thr Arg Gly Glu Pro Ser Pro Leu Val Val Glu Gly Val Ala Thr Thr
            35                  40                  45

Gly Pro Val Ala Phe Leu Phe Ala Gly Gln Gly Ser Gln Arg Val Gly
        50                  55                  60

Met Gly Arg Glu Leu Tyr Glu Ser Tyr Pro Val Phe Ala Glu Ala Phe
65                  70                  75                  80

Asp Ala Val Cys Glu Gly Phe Ala Pro Leu Pro Val Lys Asp Val Val
                85                  90                  95

Phe Gly Ala Asp Gln Glu Leu Leu Asp Arg Thr Glu Phe Ala Gln Pro
                100                 105                 110

Ala Leu Phe
        115

<210> SEQ ID NO 11
<211> LENGTH: 750
<212> TYPE: DNA
<213> ORGANISM: Streptomyces hygroscopicus

<400> SEQUENCE: 11
gatatctcca ccatccaatg ggccagcacc ggctatctgc tggccctgtc ggcggtcatc     60
```

-continued

```
ccgctcaccg gctgggccgt ggaacgcttc ggcgcccgga cgatgtggct gttctcgctg      120
accgccttcc tggccgggtc cgcgctctgc ggcgccgcgt ggtcggtcgg cagcctgatc      180
gccttccggg tcctccaggg catcggcggc ggcctgatca ccccggtgat gcagaccatc      240
ctggtccgcg cggccggtcc gcggcggatc ggccgcatca tgagcatcgt ggcggtgccc      300
ggccatctct ccccgatcgt cggtccgttg gtcggcggcg ccatcatcga ctccgtcagc      360
tggcgctgga tcttctacgt caacgtgccc atctgtgtga tcgccctgct gctggcctgg      420
cggggtgtcc cccgcgacac caggagcgac accgccgccc ggctggacgt gctcggactg      480
tcgctgctgt ccccgggctc gcggcgatca tctacggggc tgtcgcagac agcaggccga      540
gggttcgggc gacccggtcg tgtctcctgt cgctgggcgc gtctgctggc gcctcgcggc      600
cagcgctgcg cacccgatca cccgtctgaa ctgcgctgtt cggcacgcct cgtcacgccg      660
gcacgtgctg atgttctggg cgcatgttc gtcttcgggc gaatgctgct gatgccgcct       720
acctaccgac ggtccgaaca gaccgcctgg                                       750
```

<210> SEQ ID NO 12
<211> LENGTH: 153
<212> TYPE: PRT
<213> ORGANISM: Streptomyces hygroscopicus

<400> SEQUENCE: 12

```
Ile Pro Val Ala Leu Asp Asn Glu Pro Phe Gly Ser Arg Phe Pro Gln
 1               5                  10                  15

Gln Ile Gly Val Leu Gln Ser Arg Val Glu Ala Met Leu Glu Glu Arg
                20                  25                  30

Leu Glu Thr Val His Gly Ile Thr Val Glu Arg Gly Arg Glu Leu Ile
            35                  40                  45

Gly Phe Glu Gln Asp Glu His Gly Val Thr Ala Thr Val Arg Gly Pro
        50                  55                  60

Glu Gly Arg Glu Thr Leu Leu Arg Gly Arg Tyr Leu Val Gly Cys Asp
    65                  70                  75                  80

Gly Ser Arg Ser Arg Val Arg Arg Val Leu Gly Leu Pro Phe Asp Gly
                85                  90                  95

Thr Asp Gly Gly Pro Gln Thr Arg Val Ala Ala Asp Val Val Leu Val
               100                 105                 110

Arg Pro Pro Glu Lys Trp Phe Asp Gly Gln Ala Pro Gln Gly Val Gly
           115                 120                 125

Glu Val Asp Gly Arg Asp Val Arg Met Leu Pro Asp Val Gly Leu Thr
       130                 135                 140

Gly Met Ile Thr Leu Ser Glu Gly Cys
145                 150
```

<210> SEQ ID NO 13
<211> LENGTH: 561
<212> TYPE: DNA
<213> ORGANISM: Streptomyces hygroscopicus

<400> SEQUENCE: 13

```
gacacccgt cgccgccggt ggccaccagg tcccacagac cctcgggaga ctccaccccg       60
cccgggaaac ggcacgccat ccccacgatc gccaacggct catcactcgc cgccaccgca      120
cccggcggca acgccgccac ggcatccgcc tcccgccga agagctccgc acccagccgg       180
cccgccagcg ccgcgggcgt cgggtagtcg aacaccagcg tcgccggaag cctcaggccc      240
```

```
gttgccgtat ccagccggtt ccgcagttcg acggcggtca gcgagtcgaa gccgatctcc    300
cggaacgcct tgtcggcgtc cacggccgcc tcggagccgt ggccgagcgc gatcgcggcc    360
tcgtgccgca ccagctccac gaggtgtgcg gcccgctcct ccggccgagt ccggccaggc    420
gctcgcggag cgagcgggtc gcggcgctgc gcgcgggcgc gcacggtcgt acgagccgag    480
acagcgggga gtcgcgctgg tcgcgcagac gcctgtcagc gcatggcagc agaacggtgt    540
gcgagcgacg cgcacgatcc c                                              561
```

<210> SEQ ID NO 14
<211> LENGTH: 185
<212> TYPE: PRT
<213> ORGANISM: Streptomyces hygroscopicus

<400> SEQUENCE: 14

```
Gly Ser Cys Ala Ser Leu Ala His Arg Ser Ala Ala Met Arg Gln Ala
 1               5                  10                  15

Ser Ala Arg Pro Ala Arg Leu Pro Ala Val Ser Ala Arg Thr Thr Val
            20                  25                  30

Arg Ala Arg Ala Gln Arg Arg Asp Pro Leu Ala Pro Arg Ala Pro Gly
        35                  40                  45

Arg Thr Arg Pro Glu Glu Arg Ala Ala His Leu Val Glu Leu Val Arg
    50                  55                  60

His Glu Ala Ala Ile Ala Leu Gly His Gly Ser Glu Ala Ala Val Asp
65                  70                  75                  80

Ala Asp Lys Ala Phe Arg Glu Ile Gly Phe Asp Ser Leu Thr Ala Val
                85                  90                  95

Glu Leu Arg Asn Arg Leu Asp Thr Ala Thr Gly Leu Arg Leu Pro Ala
            100                 105                 110

Thr Leu Val Phe Asp Tyr Pro Thr Pro Ala Ala Leu Ala Gly Arg Leu
        115                 120                 125

Gly Ala Glu Leu Phe Gly Gly Glu Ala Asp Ala Val Ala Ala Leu Pro
    130                 135                 140

Pro Gly Ala Val Ala Ala Ser Asp Glu Pro Leu Ala Ile Val Gly Met
145                 150                 155                 160

Ala Cys Arg Phe Pro Gly Gly Val Glu Ser Pro Glu Gly Leu Trp Asp
                165                 170                 175

Leu Val Ala Thr Gly Gly Asp Gly Val
            180                 185
```

<210> SEQ ID NO 15
<211> LENGTH: 122
<212> TYPE: DNA
<213> ORGANISM: Streptomyces hygroscopicus

<400> SEQUENCE: 15

```
tatcgaagtg gcgttgttcc ggttggtgag tcctggggtg tggtcccgga ttttgtgctg     60
gggcattcgg tgggtgagtt ggctgccgcg catgtggcgg ggtgttttc gctgggggac    120 gc                                                                  122
```

<210> SEQ ID NO 16
<211> LENGTH: 40
<212> TYPE: PRT
<213> ORGANISM: Streptomyces hygroscopicus

<400> SEQUENCE: 16

```
Tyr Arg Ser Gly Val Val Pro Val Gly Glu Ser Trp Gly Val Val Pro
```

```
                1               5              10              15
          Asp Phe Val Leu Gly His Ser Val Gly Glu Leu Ala Ala Ala His Val
                              20              25              30
          Ala Gly Val Phe Ser Leu Gly Asp
                          35              40

<210> SEQ ID NO 17
<211> LENGTH: 466
<212> TYPE: DNA
<213> ORGANISM: Streptomyces hygroscopicus

<400> SEQUENCE: 17
cgggcgccgg aggcggaggt cgccgctgtc gccgcgcact gggaggcggc cggccgccgg    60
gtgaagcgcc tgcgggtcag ccacgccttc cactcgccgc tcatggacgc gatgctcgag   120
ccgttccgcc aggtcgccga agcgtgtcg tacgagcccc gcggatcgc gatcgtctcc     180 gacctgaccg gccgcgtcgt cggcgcggcc gagatcggca cggccgacta ctgggtgcgg   240
cacgtccgcg agtgcgtacg gttccacgac ggtctgagcc gactgacgg ccagggcgtc    300 gccaccttcc tggagctggg gccggccgga gtcctgtccg ccatgggcca ggagtccgtc   360
tccgcgttct gtgcgctgat tccgctgctg cgcgagggcc gcccgaggcc gactccgtgc   420
gctcggcgtc gcgccggcca tgtgcgggtg tcgcgtgact gacggc                  466

<210> SEQ ID NO 18
<211> LENGTH: 154
<212> TYPE: PRT
<213> ORGANISM: Streptomyces hygroscopicus

<400> SEQUENCE: 18

Arg Ala Pro Glu Ala Glu Val Ala Ala Val Ala Ala His Trp Glu Ala
  1               5              10              15

Ala Gly Arg Arg Val Lys Arg Leu Arg Val Ser His Ala Phe His Ser
                 20              25              30

Pro Leu Met Asp Ala Met Leu Glu Pro Phe Arg Gln Val Ala Glu Ser
             35              40              45

Val Ser Tyr Glu Pro Pro Arg Ile Ala Ile Val Ser Asp Leu Thr Gly
         50              55              60

Arg Val Val Gly Ala Ala Glu Ile Gly Thr Ala Asp Tyr Trp Val Arg
 65              70              75              80

His Val Arg Glu Cys Val Arg Phe His Asp Gly Leu Ser Arg Leu Asp
                 85              90              95

Gly Gln Gly Val Ala Thr Phe Leu Glu Leu Gly Pro Ala Gly Val Leu
            100             105             110

Ser Ala Met Gly Gln Glu Ser Val Ser Ala Phe Cys Ala Leu Ile Pro
        115             120             125

Leu Leu Arg Glu Gly Arg Pro Arg Pro Thr Pro Cys Ala Arg Arg Arg
    130             135             140

Ala Gly His Val Arg Val Ser Arg Asp Arg
145             150

<210> SEQ ID NO 19
<211> LENGTH: 459
<212> TYPE: DNA
<213> ORGANISM: Streptomyces hygroscopicus

<400> SEQUENCE: 19
attccggtgg ccctcgacaa tgagccgttc ggctcccggt tccgcagca gatcggcgtc    60
```

```
ctccagtcgc gggtggaagc gatgctcgaa gaacggctgg aaaccgtgca cggaatcacc      120
gtggagcgcg gccgggaact catcggtttc gagcaggacg agcacggcgt cacggccacc      180
gtccggggcc cggagggccg ggagacgctg ctgcgcggcc gctatctcgt ggggtgtgac      240
ggttcgcgga gcagggtgcg cagggtgctg ggcctgccgt tcgacggcac ggacggcggc      300
ccgcagaccc gggtggcggc cgatgtggtg ctggtgcggc cgcccgagaa gtggttcgac      360
ggccaggccc cgcaagggt cggcgaggtg gacggacgcg atgtccggat gctgccggac      420
gtgggactga ccgggatgat caccctgagc gagggctgc                            459

<210> SEQ ID NO 20
<211> LENGTH: 153
<212> TYPE: PRT
<213> ORGANISM: Streptomyces hygroscopicus

<400> SEQUENCE: 20

Ile Pro Val Ala Leu Asp Asn Glu Pro Phe Gly Ser Arg Phe Pro Gln
 1               5                  10                  15

Gln Ile Gly Val Leu Gln Ser Arg Val Glu Ala Met Leu Glu Glu Arg
            20                  25                  30

Leu Glu Thr Val His Gly Ile Thr Val Glu Arg Gly Arg Glu Leu Ile
        35                  40                  45

Gly Phe Glu Gln Asp Glu His Gly Val Thr Ala Thr Val Arg Gly Pro
    50                  55                  60

Glu Gly Arg Glu Thr Leu Leu Arg Gly Arg Tyr Leu Val Gly Cys Asp
65                  70                  75                  80

Gly Ser Arg Ser Arg Val Arg Val Leu Gly Leu Pro Phe Asp Gly
                85                  90                  95

Thr Asp Gly Gly Pro Gln Thr Arg Val Ala Ala Asp Val Val Leu Val
            100                 105                 110

Arg Pro Pro Glu Lys Trp Phe Asp Gly Gln Ala Pro Gln Gly Val Gly
        115                 120                 125

Glu Val Asp Gly Arg Asp Val Arg Met Leu Pro Asp Val Gly Leu Thr
    130                 135                 140

Gly Met Ile Thr Leu Ser Glu Gly Cys
145                 150

<210> SEQ ID NO 21
<211> LENGTH: 190
<212> TYPE: DNA
<213> ORGANISM: Streptomyces hygroscopicus

<400> SEQUENCE: 21
aattcgcggc cgcataatac gactcactat agggatcgcc ttctgctgcg cgccgtgct      60 gcttccgggg gcgctcctgg cgggctgacc gttacttcgt tgcagaggaa agcgatgacc     120
gagccagcag aaccccagta cccgcaggcc ccgccaccga cctacccaca agccccgcca     180
ccggcctacc                                                           190

<210> SEQ ID NO 22
<211> LENGTH: 63
<212> TYPE: PRT
<213> ORGANISM: Streptomyces hygroscopicus

<400> SEQUENCE: 22

Asn Ser Arg Pro His Asn Thr Thr His Tyr Arg Asp Arg Leu Leu Leu
 1               5                  10                  15
```

Arg Arg Arg Ala Ala Ser Arg Gly Ala Pro Gly Leu Thr Val Thr
            20                  25                  30

Ser Leu Gln Arg Lys Ala Met Thr Glu Pro Ala Glu Pro Gln Tyr Pro
        35                  40                  45

Gln Ala Pro Pro Thr Tyr Pro Gln Ala Pro Pro Ala Tyr
    50                  55                  60

<210> SEQ ID NO 23
<211> LENGTH: 792
<212> TYPE: DNA
<213> ORGANISM: Streptomyces hygroscopicus

<400> SEQUENCE: 23
gaccgcagct ggggcgtggc cctcggcgcg ccgctgggca tcctgctcca ggccatgacc      60
tccctgggac gccatgccga ggccgaggaa ctgacccggg cggcgccgcc ggagctgttc     120
cagacccgct gggggctgct gtacctgtac gcccgggccc ggtaccacct ggcggccaac     180
cggctccagg ccgggctgag cgacctcacc acctgcggtg agctcatgac cgcctgggac     240
atggacctgc cgggcttcat ccctggcgcg ccgacgccg cgcggatcca tctgcggctg     300
gggaacgtac ggcaggcccg gcggctggcc gaggagcagc tggcccggcc cctcaccacg     360
ggctcccgca cccatggcat cgccctgcgc acgctggcgg cctgtagtga gctcaaacag     420
cggccccacc tgctgcgcaa ggccgccgag gagctccagg agcatggcga ccgactggag     480
ctgcggagac ctcaccgatc tcagcgaggc cactacgcgc tggcgagttc gacggggccg     540
gatgatggcg cgcatggcat gcacgtggca cgagtgcgta cggacgcgct gcgcagcgct     600
gtcgtgtgct gctgagagac tcgagcgctg atcgacccgc ggggtacggc tgacgatgcg     660
actgcgggtg tcggcctgcc gtcagggaca gcagcggtga tcgcgccagc ttattacgta     720
cgcggtgact gcatgacagc atgcagctga cgtacacagg gtatgcgttg ctcactacgg     780
ccaatacggt gg                                                         792

<210> SEQ ID NO 24
<211> LENGTH: 262
<212> TYPE: PRT
<213> ORGANISM: Streptomyces hygroscopicus

<400> SEQUENCE: 24

Asp Arg Ser Trp Gly Val Ala Leu Gly Ala Pro Leu Gly Ile Leu Leu
 1               5                  10                  15

Gln Ala Met Thr Ser Leu Gly Arg His Ala Glu Ala Glu Glu Leu Thr
            20                  25                  30

Arg Ala Ala Pro Pro Glu Leu Phe Gln Thr Arg Trp Gly Leu Leu Tyr
        35                  40                  45

Leu Tyr Ala Arg Gly Arg Tyr His Leu Ala Ala Asn Arg Leu Gln Ala
    50                  55                  60

Gly Leu Ser Asp Leu Thr Thr Cys Gly Glu Leu Met Thr Ala Trp Asp
65                  70                  75                  80

Met Asp Leu Pro Gly Phe Ile Pro Trp Arg Ala Asp Ala Ala Arg Ile
                85                  90                  95

His Leu Arg Leu Gly Asn Val Arg Gln Ala Arg Arg Leu Ala Glu Glu
            100                 105                 110

Gln Leu Ala Arg Pro Leu Thr Thr Gly Ser Arg Thr His Gly Ile Ala
        115                 120                 125

Leu Arg Thr Leu Ala Ala Cys Ser Glu Leu Lys Gln Arg Pro His Leu

```
        130              135              140
Leu Arg Lys Ala Ala Glu Glu Leu Gln Glu His Gly Asp Arg Leu Glu
145             150                 155                 160

Leu Arg Arg Pro His Arg Ser Gln Arg Gly His Tyr Ala Leu Ala Ser
                165                 170                 175

Ser Thr Gly Pro Asp Asp Gly Ala His Gly Met His Val Ala Arg Val
            180                 185                 190

Arg Thr Asp Ala Leu Arg Ser Ala Val Val Cys Cys Glu Thr Arg Ala
        195                 200                 205

Leu Ile Asp Pro Arg Gly Thr Ala Asp Asp Ala Thr Ala Gly Val Gly
    210                 215                 220

Leu Pro Ser Gly Thr Ala Ala Val Ile Ala Pro Ala Tyr Tyr Val Arg
225                 230                 235                 240

Gly Asp Cys Met Thr Ala Cys Ser Arg Thr Gln Gly Met Arg Cys Ser
                245                 250                 255

Leu Arg Pro Ile Arg Trp
            260
```

<210> SEQ ID NO 25
<211> LENGTH: 818
<212> TYPE: DNA
<213> ORGANISM: Streptomyces hygroscopicus

<400> SEQUENCE: 25

```
gaattcccac gggacgaggt ggccatgacc gtgcaagccc ccgaagcacc gttgcgcgaa      60
ctcacgaatg aggaggtggc cgcctaccgg gaggacggcg ccatacgagc gtcgggactg     120
ttctccgagg agtgggtggc ccggataacg gaggccgtcg actacgtcct ggccaatccc     180
tccgtactgg cgcaggcgac cgccgacttc tccgagggaa aggcgaacgg cgacgctttc     240
atgtggaaga cacatgaggc attccgtgat ttcgtcttcc gctcaccggc ctcccgggtc     300
gcccagcggc tcttcggctc acagaccgtc accgccttct acgaccaggt gttcaccaag     360
ccgcggggca ccgcgaagcc cactccgttc acgaggacg ccacgtcctt ccccatcgac     420
ggggaccagg tctgcgcgat gtggatcgcc ctggaccact gcggtcccga acggccgcc     480
ctgaccgtcg tccgtggctc gcaccgctgg ggagcgggac ccgggcccgg tcacctccag     540
cctgatgcac ccgggcatgc aggcggggca gaacacaccc gaggcgggga cgcacccgag     600
tcggggggcc gagccgagtc gggggcgga ccgccgtccg aaaccgcggg acgtgctcac     660
ctgggacgaa gaggacctgc ctccgcctgg gatctggccc cgcaagccgg tcattttcac     720
ccgcccgccc tgacgggtta ccggaccgcc cggcagggcg cgggcttgtt ccgctggctg     780
gccacggctt acctcagccg aggctatgca tcgtggac                             818
```

<210> SEQ ID NO 26
<211> LENGTH: 272
<212> TYPE: PRT
<213> ORGANISM: Streptomyces hygroscopicus

<400> SEQUENCE: 26

```
Glu Phe Pro Arg Asp Glu Val Ala Met Thr Val Gln Ala Pro Glu Ala
1               5                   10                  15

Pro Leu Arg Glu Leu Thr Asn Glu Glu Val Ala Ala Tyr Arg Glu Asp
            20                  25                  30

Gly Ala Ile Arg Ala Ser Gly Leu Phe Ser Glu Glu Trp Val Ala Arg
        35                  40                  45
```

```
Ile Thr Glu Ala Val Asp Tyr Val Leu Ala Asn Pro Ser Val Leu Ala
 50                  55                  60

Gln Ala Thr Ala Asp Phe Ser Glu Gly Lys Ala Asn Gly Asp Ala Phe
 65                  70                  75                  80

Met Trp Lys Thr His Glu Ala Phe Arg Asp Phe Val Phe Arg Ser Pro
                 85                  90                  95

Ala Ser Arg Val Ala Gln Arg Leu Phe Gly Ser Gln Thr Val Thr Ala
            100                 105                 110

Phe Tyr Asp Gln Val Phe Thr Lys Pro Arg Gly Thr Ala Lys Pro Thr
        115                 120                 125

Pro Phe His Glu Asp Ala Thr Ser Phe Pro Ile Asp Gly Asp Gln Val
    130                 135                 140

Cys Ala Met Trp Ile Ala Leu Asp His Cys Gly Pro Glu Thr Ala Ala
145                 150                 155                 160

Leu Thr Val Val Arg Gly Ser His Arg Trp Gly Ala Gly Pro Gly Pro
                165                 170                 175

Gly His Leu Gln Pro Asp Ala Pro Gly His Ala Gly Gly Ala Glu His
            180                 185                 190

Thr Arg Gly Gly Asp Ala Pro Glu Ser Gly Gly Arg Ala Glu Ser Gly
        195                 200                 205

Gly Gly Pro Pro Ser Glu Thr Ala Gly Arg Ala His Leu Gly Arg Arg
    210                 215                 220

Gly Pro Ala Ser Ala Trp Asp Leu Ala Pro Gln Ala Gly His Phe His
225                 230                 235                 240

Pro Pro Ala Leu Thr Gly Tyr Arg Thr Ala Arg Gln Gly Ala Gly Leu
                245                 250                 255

Phe Arg Trp Leu Ala Thr Ala Tyr Leu Ser Arg Gly Tyr Ala Ser Trp
            260                 265                 270

<210> SEQ ID NO 27
<211> LENGTH: 577
<212> TYPE: DNA
<213> ORGANISM: Streptomyces hygroscopicus

<400> SEQUENCE: 27
tatcggtgtc gaactcgtgc gacaggccgt cgatcgcgac gctgacgatc gtggtgtcca    60
gcatcgacgc gatcgcgccg atcaccagga tcacgcccag tcggatgagt gcgggtccag   120
gccggtcgga tgcggattgc tcggggggcgg aagaaggggc cccgtggac gggctagtca   180 tgcgagggac tctacaccgt gtggtgtagt tgctgtatcc tcctgttctg tggttaccaa   240
tgcacggact tccgccgttg tcggcgcgcg cactcccgcc gactcgcgca ctcccgccgg   300
cgccggcaag cggctgcgcc agggtcccc gaagaagcgc gcggcgatcg cacgggcggc    360
gttcgagctg ttcgtggccc aaggcgtcgc cggcaccagc gtcgatgcca tcgccgcga   420 agcgggcgtc tccagcgcac cgtctacgac tactacggca gcaggagcgg ctctcctctc   480
cgtcatcgag acgcgagcgc gtacgcgaca gtcgcggaca tctggacgca cctcgcgagt   540
cgacggcacg atgcatcgcg cacgacgact cagcggg                             577

<210> SEQ ID NO 28
<211> LENGTH: 753
<212> TYPE: DNA
<213> ORGANISM: Streptomyces hygroscopicus

<400> SEQUENCE: 28
atcccgaaga actccgcgtc gaagtctccg gcgccgttca cgaagccgcc ctcgcggacg    60
```

-continued

```
tacgaggtac cggggtggtc ggggtccggg tggtacaggg cgtccatgtc ccagccccgg      120
tcggtgggga acgcggtcat cccgtcacgg ccctcggcca ccagccgcca caggtcttcg      180
ggcgactcca catcgcccgg gaggcggcag gccatcgcca cgatcgcgat ggggtcatca      240
tcggcgacgg ccaccgccgt ggcctcggtg acgtcctccg caccgagcaa ctcggcgcgc      300
aggtgctggg ccagcgcgtt cggcgagggg tggtcgaaga cgagggtggc gggcagccgc      360 agcccgtgg cggcgttcag ccggttgcgg agttccacgg ccgtgagcga gtcgaagcca      420
gctccttgaa cgccttcgtc gcgttcacgg cttcctgcga ggtgtgccga gcacggcggc      480
acgtcggcgc gtacaggtcc agcaggatgc gcggctcgct cggacgcggc ggcagcggcg      540
tgcagcgcga gcccggcgcc gtgcgtacga cgcgcgacgc gcggacgtgg cgtacagccc      600
tgaacgcgcg gagccaccgt ctgcgacgcc ggcagtcagt gagggaccga ccgtgttcgg      660
cagccgctga cggtcaacgt catcaatgca tgtggacatc ccgctatcg gcgattcgct      720 tcaagtcgga tcagtactcg tcaggcagaa gag                                   753

<210> SEQ ID NO 29
<211> LENGTH: 785
<212> TYPE: DNA
<213> ORGANISM: Streptomyces hygroscopicus

<400> SEQUENCE: 29
gcggccgcat aatacgactc actatagga tcttcttccc ggccagcaac atgcccagtc       60
cgagggcgag tttcgccttc ttcgtgcgcc caaggagata gcctcccgtg atcgcgaccg     120
cgatcttgcc gtttgtcatc atcaattcgc tcccgaagtc gaacgcggct tcgatgtgga     180
cggccgggta cccacatacg gaaaagcccc actcgtcaaa agacgagtgg ggcttttgtg     240
ctccggggag cgtcaggtca cttgacgatc ttggtgacct ggccggcgcc gacggtccgg     300
ccaccctcac ggatggcgaa cttcaggccc tcctccatgg cgaccggctg atcagctgg      360 acggacatct cggtgttgtc gcccggcatg accatctcgg tgccctcggg gagggtcaca     420
acgcccgtca cgtccgtggt acggaagtag aactgcggac ggtagttgtt gaagaacggc     480
gtgtggcggc caccctcgtc ctggacagga tgtacgcctg gcctcgaact cgggtgtgcg     540
gggtgaccga gcccggctga tgatgacctg gcgcgctcga cgttctcacg ctgatgcgcg     600
agcagcagaa cgacgtctca ccgggcctgc cctcgttcga gccagcctgc ggacattccg     660
atccggtgac ggtggtcgag ggtctctccg gctgatgcga tgatgttgac gtttcgttga     720
cctcagcacg ccggactgat cgcgggtgac aacgatccga cggtatggta aacgttcgta     780
atcgg                                                                 785

<210> SEQ ID NO 30
<211> LENGTH: 828
<212> TYPE: DNA
<213> ORGANISM: Streptomyces hygroscopicus

<400> SEQUENCE: 30
cctctccgca cccgtccctc ccctcacctc atctcgtggc cccggctcgc ctaagtcgcc      60
cctggccgcc cgcctcccct ttgcctctcc ctctctctgg cgggtggggg ggggggggtt     120
cccccctttt tgccttgccc cacctccgtg ggggcttggg aaattgtttt tttttccatg     180
cactcagtta tagggccaga aattgggtca ctggccccc ccatcggagg tcagagtgta     240
tcgataagct tgaatatcca ggcccgacca actatctctt gggttgggca gccggttgac     300
```

-continued

```
ttcacgtggc agacggcagg gccgattgtt gttcgcgcat caccgttgga ggagcagggc    360
tacatcttcg tcaatcgcgg cggtcttggc cgggcttgga caccccttggc ggaaccggtc   420 cacatcggcg gaaagcttgc cggaggtcgc ctaacgacac gatcgccctc gccgattatt    480
gaacgccgac ggcaagaccg acatcatcgg ccggcagggc ggcaccagca agatcgacat    540
cattcccttc gcgggcgagg tcgacggcac caacagcttc aacgcgcccg agcggctggg    600
ccaccctccg gcgcagacgt gacattcccc ctggggcgcc gccgacattc accggcttcc    660
gtgccgtgcc cgagcttgct tcgtcctggc aacgacaacg tgcgaacctt cgcccagtcc    720 caaccttcc cttcaccgtg aaaccatgtg gcacgtggaa ccgcacgaac gtgtgtgaag     780
cacctgggtg gtggcagaaa tgtcagaact ggtgcaacaa ccgaatca                 828
```

<210> SEQ ID NO 31
<211> LENGTH: 718
<212> TYPE: DNA
<213> ORGANISM: Streptomyces hygroscopicus

<400> SEQUENCE: 31

```
gatatcggcg ccgatcttca cgggttcacc atacgtcttc aatccattga gcgcaccgga    60
acccggatag acaaataatt cactgccatg ccggacgaga atatcctgct tgccgtcgcc    120
gtcgaacgaa ccggaatgac cggtataggt cagcattgac tctccccgct ccagggttcg    180
ataagcgccc ccgcaaagga attaccgagg agcgcgccgc cagcatttag ccatcctacg    240
gacgctattc atccggtaaa cccctagacc aacccctagg gctccagatg atgagacacc    300
acgtgttgac agcggccgcc ccgggctcca acctgatgac gtcaccgcag gtcagcacgg    360
attcccccag gaaaccccag ccagctccgc ggcggtcggc gaccgctccg gtgcggcggg    420
ccgaccggat gaatgcccac ttcaggcccg cggtgcgatg aacgtcacgt tttccgtacg    480
acatgtccgc gccgtccgga aataatgtga gatggcggca catactgcca cccattagta    540
tggatcagta ggcgctcttt tttcgctgac gttctgtgac agcccacacc atcgagagcg    600
gcgcagacag tgcatcgcgc atgcattcgc gcacgacgag actccacgag gggattgtgg    660
agctggcgac ggatgaccga actcactcgg ctacgatcat gcggtcgacc tgcatggt     718
```

POLYKETIDE SYNTHASE ENZYMES AND RECOMBINANT DNA CONSTRUCTS THEREFOR

FIELD OF THE INVENTION

The present invention relates to polyketides and the polyketide synthase ("PKS") enzymes that produce them. The invention also relates generally to genes encoding PKS enzymes and to recombinant host cells containing such genes and in which expression of such genes leads to the production of polyketides. Thus, the invention relates to the fields of chemistry, molecular biology, and agricultural, medical, and veternary technology.

Polyketides are a large and diverse group of biologically active molecules. Tetracycline, erythromycin, epotilone, FK-506, FK-520, narbomycin, picromycin, rapamycin, spincoyn, and tylosin, are examples of such compounds. Given the difficulty in producing polyketide compounds by traditional chemical methodology, and the typically low.expression of polyketides in wild-type cells, there has been considerable interest in finding improved or alternate means to produce polyketide compounds.

This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. The present invention provides methods and reagents relating to the PKS gene cluster for the FK-520 polyketide.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. See, e.g., PCT publication Nos. WO 93/13663; WO 95/08548; WO 96/40968; 97/02358; and 98/27203; U.S. Pat. Nos. 4,874,748; 5,063,155; 5,098,837; 5,149,639; 5,672,491; and 5,712,146; and Fu et al., 1994, *Biochemistry* 33: 9321–9326; McDaniel et al., 1993, *Science* 262: 1546–1550; and Rohr, 1995, *Angew. Chem. Int. Ed. Engl.* 34(8): 881–888, each of which is incorporated herein by reference.

Polyketides are synthesized in nature by PKS enzymes. These enyzmes, which are complexes of multiple large proteins, are similar to, but distinct from, the synthases which catalyze condensation of 2-carbon units in the biosynthesis of fatty acids. PKS enzymes are encoded by "PKS gene clusters." PKS gene clusters usually consist of three or more open reading frames ("ORFs"), each comprising two or more "modules" of ketosynthase activity, each module of which consists of at least two (if a starter unit) and more typically three or more enzymatic activities or "domains." Two major types of PKS enzymes are known; these differ in their composition and mode of synthesis of the polyketide synthesized. These two major types of PKS enzymes are commonly referred to as Type I or "modular" and Type II "aromatic" PKS enzymes.

The FK-520 PKS enzyme is a member of the Type I or modular PKS enzyme group. In this type, a set of separate catalytic active sites (each active site is termed a "domain", and a set thereof is termed a "module") exists for each cycle of carbon chain elongation and modification in the polyketide synthesis pathway. The active sites and modules of a typical Type I PKS enzyme are shown in FIG. 9 of PCT patent publication No. WO 95/08548, which depicts a model of 6-deoxyerythronolide B synthase ("DEBS"), which is involved in the synthesis of erythromycin. Six separate modules, each catalyzing a round of condensation and modification of a 2-carbon unit, are present in DEBS. The number and type of catalytic domains that are present in each module varies, and the total of 6 modules is provided on 3 separate proteins (designated DEBS-1, DEBS-2, and DEBS-3, with 2 modules per protein). Each of the DEBS polypeptides is encoded by a separate open reading frame (ORF). See Caffrey et al., 1992, *FEBS Letters* 304: 205, incorporated herein by reference. The catalytic domains of the DEBS polypeptides provide a representative example of Type I PKS structure. In this particular case, modules 1 and 2 reside on DEBS-1, modules 3 and 4 on DEBS-2, and modules 5 and 6 on DEBS-3; module 1 is the first module to act on the growing polyketide backbone, and module 6 the last.

A typical (non-starter) minimal Type I PKS module is typified by module 3 of DEBS, which contains a ketosynthase ("KS") domain, an acyltransferase ("AT") domain, and an acyl carrier protein ("ACP") domain. These three enzyme activities are sufficient to activate the 2-carbon extender unit and attach it to the growing polyketide molecule. Additional domains that may be included in a module relate to reactions other than the actual condensation, and include a ketoreductase activity ("KR") activity, a dehydratase activity ("DH"), and an enoylreductase activity ("ER"). With respect to DEBS-1, the first module thereof also contains repeats of the AT and ACP activities because it catalyzes initial condensation, i.e. it begins with a "loading domain" represented by AT and ACP, which determine the nature of the starter unit.

The "finishing" of the 6-deoxyerythronolide molecule is regulated by a thioesterase ("TE") activity in module 6. The TE activity catalyzes cyclization of the macrolide ring by formation of an ester linkage. In FK-506, FK-520, rapamycin, and similar polyketides, the ester linkage formed by the TE activity is replaced by a linkage formed by incorporation of a picolate acid residue. The enzymatic activity that catalyzes this incorporation for the rapamycin enzyme is known as rapP.

In PKS polypeptides, the regions that encode enzymatic activities (domains) are separated by linker or "scaffold"-encoding regions. These scaffold regions encode amino acid sequences that space the enzymatic activities (domains) at the appropriate distances and in the correct order. Thus, the linker regions of a PKS protein collectively can be considered to encode a scaffold into which the various domains (and thus modules) are placed in a particular order and spatial arrangement. Generally, this organization permits PKS domains of different or identical substrate specificities to be substituted (usually at the DNA level) between PKS enzymes by various available methodologies. Thus, there is considerable flexibility in the design of new PKS enzymes with the result that known polyketides can be produced more effectively, and novel polyketides useful as pharmaceuticals or for other purposes can be made.

Additional structural complexity in the resultant polyketides arises from or can be introduced by various activities, including glycosylation, hydroxylation, methylation, and other enzymatic activities. The rapP enzymatic activity mentioned above is an example of one such activity; another example is the hydroxylation of a polyketide by an oxidase enzyme similar in structure and function to the cytochrome P450 oxidase enzyme. By appropriate application of recombinant DNA technology, a wide variety of polyketides can be prepared in a variety of different host cells provided one has access to nucleic acid compounds that encode PKS proteins and polyketide modification enzymes. The present invention helps meet the need for such nucleic acid compounds by providing recombinant vectors that encode a PKS enzyme and various polyetide modification enzymes from an FK-520 producing strain of *Streptomyces hygroscopicus.*

SUMMARY OF THE INVENTION

The present invention provides recombinant DNA vectors that encode a PKS enzyme and various polyketide modification enzymes from an FK-520 producing strain *Streptimyces hygroscopicus*. Illustrative vectors of the invention include cosmid 34–183, 34–122, and 34–126.

The present invention also provides nucleic acid compounds that encode the various domains of the FK-520 PKS, i.e., the KS, AT, ACP, and other domains. These compounds can be readily used, alone or in combination with other PKS of the invention domain coding sequences, as intermediates in the construction of recombinant vectors that encode PKS enzymes that make novel polyketides.

In one embodiment, the invention provides an isolated nucleic acid that encodes an activity of a polyketide synthase enzyme that synthesizes polyketide FK-520. The encoded activity can be a ketosynthase activity, an acyltransferase activity, or an acyl carrier protein activity. In another aspect, the invention provides an isolated nucleic acid that encodes a module, said module comprising a ketosynthase activity, an acyl transferase activity, and an acyl carrier protein activity. In another aspect, the invention provides an isolated nucleic acid that encodes an open reading frame, said open reading frame comprising two or more modules. In another aspect, the invention provides an isolated nucleic acid that encodes a gene cluster, said gene cluster comprising two or more open reading frames. In another aspect, these isolated nucleic acids are incorporated within a recombinant expression vector.

In another embodiment, the invention provides an isolated nucleic acid that encodes a module in which at least one of the activities in the module is an activity of a non-FK-520 polyketide synthase. In one aspect, the invention provides an isolated nucleic acid that encodes an open reading frame comprising two or more modules, in which at least one of said modules is a module comprising an activity of a non-FK-520 polyketide synthase. In one aspect, the non-FK-520 polyketide synthase is rapamycin polyketide synthase, FK-506 polyketide synthase, or erythromycin polyketide synthase. In another aspect, these isolated nucleic acids are incorporated within a recombinant expression vector.

In another embodiment, the invention provides a method of preparing a polyketide, said method comprising transforming a host cell with a recombinant DNA vector that encodes a module of a polyketide synthase, said module comprising at least one FK-520 polyketide synthase activity, and culturing said host cell under conditions such that said polyketide synthase is produced and catalyzes synthesis of said polyketide. In one aspect, the method is practiced with a Streptomyces host cell. In another aspect, the polyketide produced is FK-520. In another aspect, the polyketide produced is a polyketide related in structure to FK-520. In another aspect, the polyketide produced is a polyketide related in structure to FK-506 or rapamycin.

These and other embodiments and aspects of the invention will be more fully understood after consideration of the attached Drawing and its brief description below, together with the detailed description, example, and claims that follow.

DETAILED DESCRIPTION OF THE INVENTION

Figure 1:
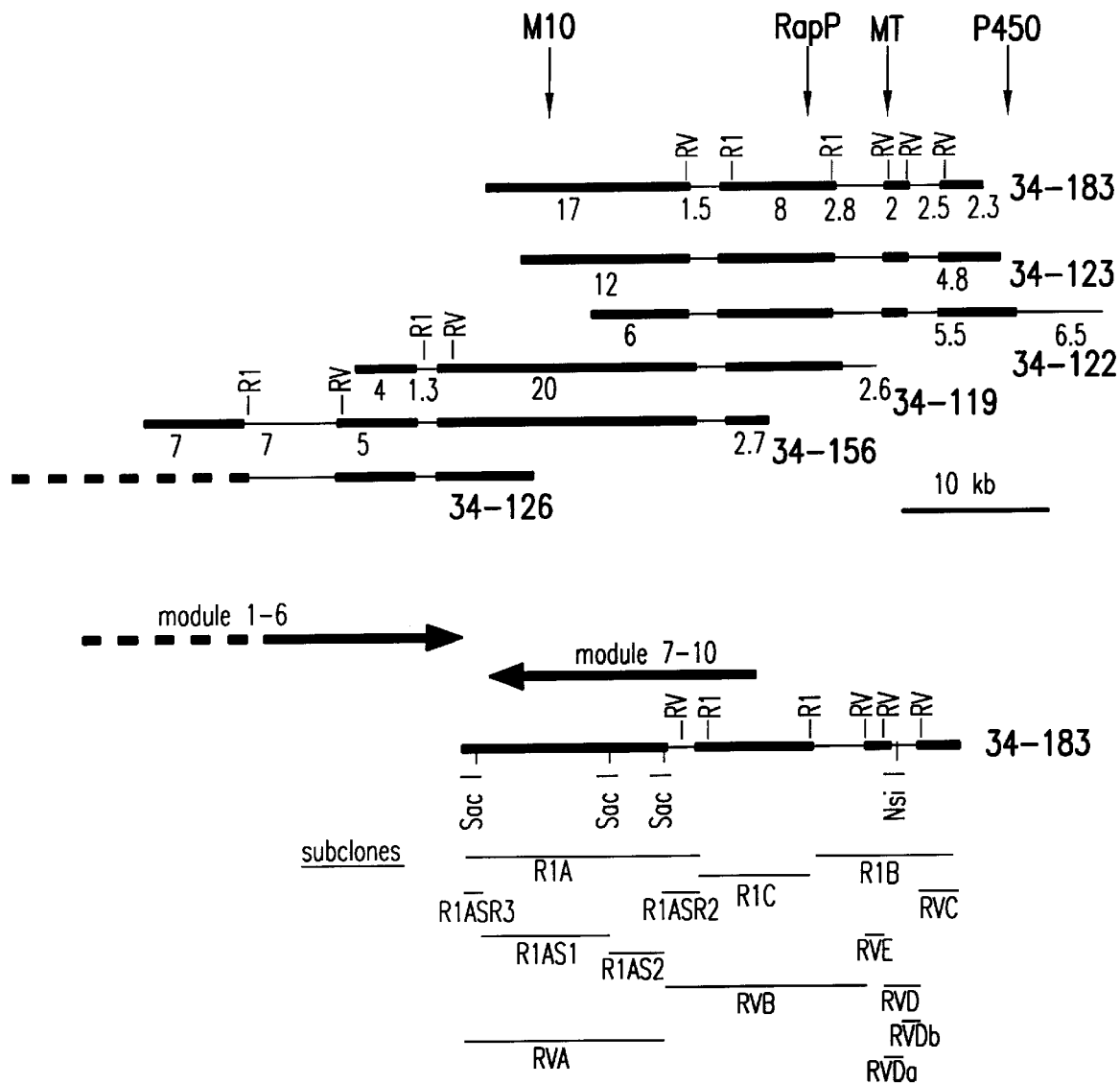
FIG. 1 shows restriction site and function maps of the insert DNA in various cosmids of the invention. The different cosmid inserts are identified with a reference number assigned to each cosmid, i.e., cosmid 34–183, cosmid 34–123. Various restriction sites (SacI, NsiI) are also shown (RV is EcoRV; and R1 is EcoRI). The location of the coding sequences for modules 1–10 of FK-520 PKS are labeled (M10 is module 10), as is the location of the coding sequences for the methyltransferase enzyme ("MT"), the rapP homologue enzyme, and the P450 homologue enzyme. The sizes (in kilobase (kb) pairs) of various portions of the inserts are also shown, as are various subclones of cosmid 34–183.

Given the valuable pharmaceutical properties of polyketides, there is a need for methods and reagents for producing large quantities of polyketides, as well as for producing related compounds not found in nature. The present invention provides such methods and reagents, with particular application to methods and reagents for producing the polyketide known as FK-520, also known as ascomycin or L-683,590. See Holt et al., 1993, JACS 115:9925. The present invention also provides methods and reagents for making novel polyketides related in structure to FK-520, FK-506, rapamycin, and structurally related polyketides.

The FK-506 and rapamycin polyketides are potent immunosuppressants, with chemical structures shown below.

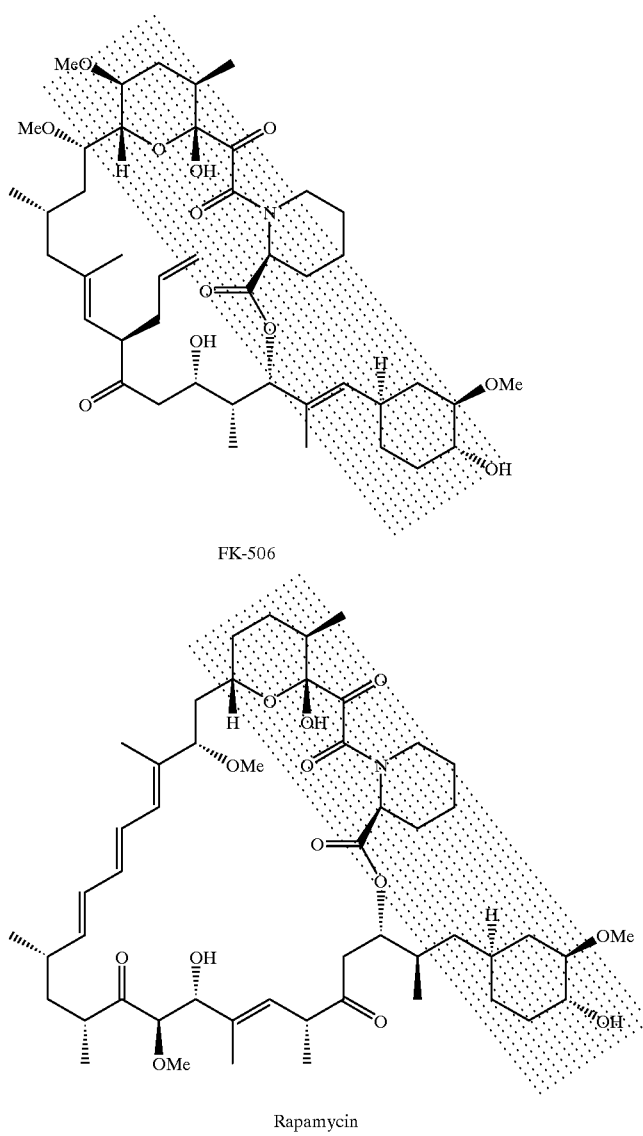

FK-506

Rapamycin

FK-520 differs from FK-506 in that it lacks the allyl group of FK-506 and has reduced immnunosuppressive activity.

These compounds act through initial formation of an intermediate complex with a protein "immunophilin" known as FKBP-12 (FK-506 binding protein). Immnunophilins are a class of cytosolic proteins that form complexes with molecules such as FK-506, FK-520, and rapamycin that in turn serve as ligands for other cellular targets involved in signal transduction. Binding of FK-506d FK-520, and rapamycin to FKBP occurs through the structurally similar segments of the polyketide molecules, known as the "FKBP-binding domain" (shaded regions in the structures above). The FK-506-FKBP complex then binds calcineurin, while the rapamycin-FKBP complex binds to a protein known as RAFT-1. Binding of the FKBP-polyketide complex to these second proteins occurs through the dissimilar regions of the drugs known as the "effector"domains.

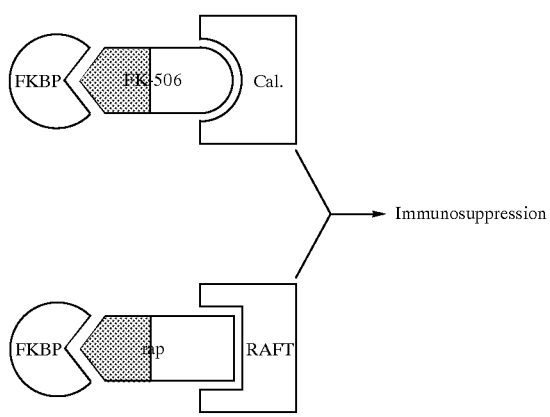

The three component FKBP-polyketide-effector complex is required for signal transduction and subsequent immunosuppressive activity of FK-506, FK-520, or rapamycin. Modifications in the effector domains of either FK-506, FK-520, or rapamycin which destroy binding to the effector proteins (calcineurin or RAFT) leads to loss of immunosuppressive activity, even though FKBP binding is unaffected. Further, such analogs antagonize the immunosuppressive effects of the parent polyketides since they compete for FKBP. Such non-immunosuppressive analogs also show reduced toxicity (see Dumont et al., 1992, *Journal of Experimental Medicine* 176, 751–760), indicating that much of the toxicity of these drugs is not linked to FKBP binding.

In addition to immunosuppressive activity, FK-520, FK-506, and rapamycin each has neuroimmunophilin activity. In the central nervous system and in peripheral nerves, immunophilins are referred to as "neuroimmunophilins". The neuroimmunophilin FKBP is markedly enriched in the central nervous system and in peripheral nerves. Molecules which bind to the neuroimmunophilin FKBP, such as FK-506 and FK-520, have the remarkable effect of stimulating nerve growth. In vitro, they promote neurite outgrowth in NGF-treated PC12 cells and in sensory neuronal cultures, and in intact animals, they promote regrowth of damaged facial and sciatic nerves, and repair lesioned serotonin and dopamine neurons in the brain. See Lyons et al., 1994, *Proc. National Academy of Science* 91: 3191–3195; Gold et al., 1995, *Journal of Neuroscience* 15: 7509–7516; and Steiner et al., 1997, *Proc. National Academy of Science* 94: 2019–2024. Further, restored central and peripheral neurons appear to be functional.

Compared to protein neurotrophic molecules (BNDF, NGF, etc.), the small-molecule neurotrophins such as FK-506, FK-520, and rapamycin have different, and often advantageous, properties. First, whereas protein neurotrophins are difficult to deliver to their intended site of action and may require intra-cranial injection, the small-molecule neurotrophins display excellent bioavailability; they are active when administered subcutaneously and orally. Second, whereas protein neurotrophins show quite specific effects, the small-molecule neurotrophins show rather broad effects. Finally, whereas protein neurotrophins often show effects on normal sensory nerves, the small-molecule neurotrophins do not induce aberrant sprouting of normal neuronal processes and seem to affect damaged nerves specifically. Neuroimmunophilin ligands have potential therapeutic utility in a variety of disorders involving nerve degeneration (e.g. multiple sclerosis, Parkinson's disease, Alzheimer's disease, stroke, traumatic spinal cord and brain injury, peripheral neuropathies).

Recent studies have shown that the immunosuppressive and neurite outgrowth activities of FK-506, FK-520, and rapamycin can be separated; the neuroregenerative activity in the absence of immunosuppressive activity is retained by agents which bind to FKBP but not to the effector proteins, calcineurin or RAFT. See Steiner et al., 1997, *Nature Medicine* 3: 421–428.

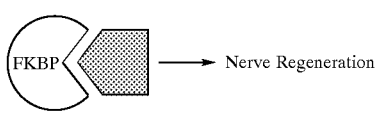

Available structure-activity data show that the important features for neurotrophic activity of rapamycin, FK-520, and FK-506 lie within the common, contiguous segments of the macrolide ring that bind to FKBP. This portion of the molecule is termed the "FKBP binding domain" (see VanDuyne et al., 1993, *Journal of Molecular Biology* 229: 105–124.). Nevertheless, the effector domains of the parent macrolides contribute to conformational rigidity of the binding domain and thus indirectly contribute to FKBP binding.

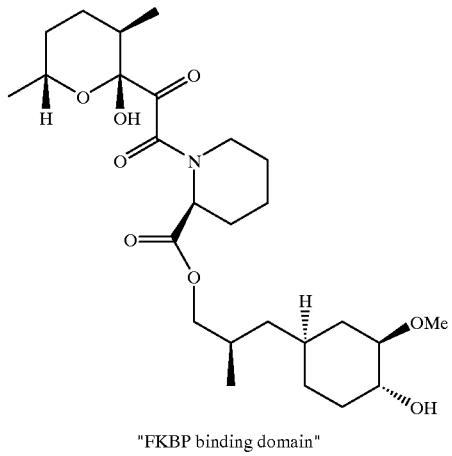

"FKBP binding domain"

There are a number of other reported analogs of FK-506, FK-520, and rapamycin that bind to FKBP but not the effector proteins calcineurin or RAFT. These analogs show effects on nerve regeneration without immunosuppressive effects.

Naturally occurring FK-520 and FK-506 analogs include the antascomycins, which are FK-506-like macrolides that lack the functional groups of FK-506 which bind to calcineurin (see Fehr et al., 1996, *The Journal of Antibiotics* 49: 230–233). These molecules bind FKBP as effectively as does FK-506; they antagonize the effects of both FK-506 and rapamycin, yet lack immunosuppressive activity.

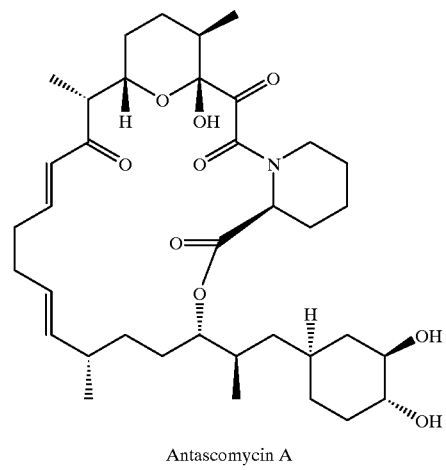

Antascomycin A

Other analogs can be produced by chemically modifying FK-506, FK-520, or rapamycin. One approach to obtaining neuroimmunophilin ligands is to destroy the effector binding region of FK-506, FK-520, or rapamycin by chemical modification. While the chemical modifications which are permitted on the parent compounds are quite limited, some useful chemically modified analogs exist. The FK-506 analog L-685,818 (ED50=0.7 nM for FKBP binding; see Dumont et al., 1992), and the rapamycin analog WAY-124, 466 ($IC_{50}$=12.5 nM; see Ocain et al., 1993, *Biochemistry Biophysical Research Communications* 192: 1340–134693)

are about as effective as FK-506, FK-520, and rapamycin at promoting neurite outgrowth in sensory neurons (see Steiner et al., 1997).

groups has produced analogs showing selective loss of immunosuppressive activity while retaining FKBP-binding (see Luengo et al., 1995, *Chemistry & Biology* 2: 471–481).

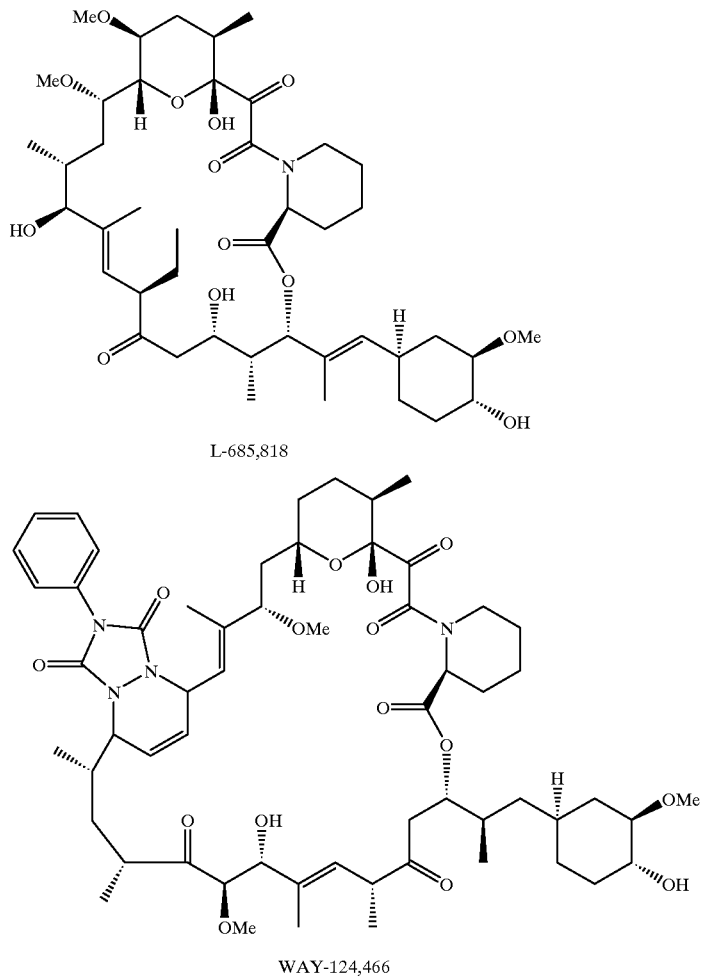

One of the few positions of rapamycin that is readily amenable to chemical modification is the allylic 16-methoxy group; this reactive group is readily exchanged by acid-catalyzed nucleophilic substitution. Replacement of the 16-methoxy group of rapamycin with a variety of bulky groups has produced analogs showing selective loss of immunosuppressive activity while retaining FKBP-binding (see Luengo et al., 1995, *Chemistry & Biology* 2: 471–481).

One of the best compounds, 1, below, shows complete loss of activity in the splenocyte proliferation assay with only a 10-fold reduction in binding to FKBP.

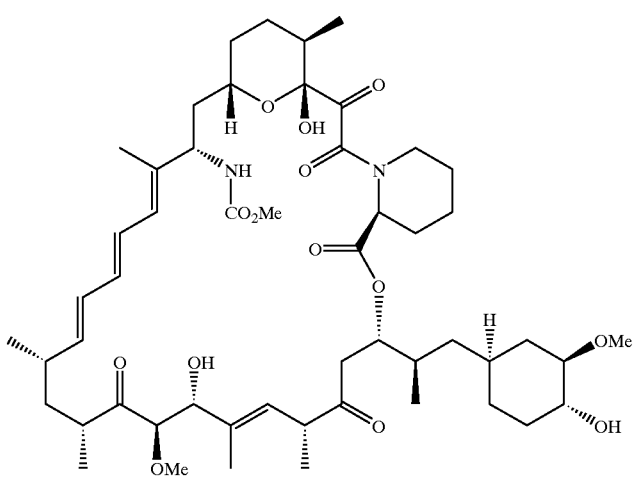

1

There are also synthetic analogs of FKBP binding domains. These compounds reflect an approach to obtaining neuroimmunophilin ligands based on "rationally designed" molecules that retain the FKBP-binding region in an appropriate conformation for binding to FKBP, but do not possess the effector binding regions. In one example, the ends of the FKBP binding domain were tethered by hydrocarbon chains (see Holt et al., 1993, *Journal of the American Chemical Society* 115: 9925–9938); the best analog, 2, below, binds to FKBP about as well as FK-506. In a similar approach, the ends of the FKBP binding domain were tethered by a tripeptide to give analog 3, below, which binds to FKBP about 20-fold poorer than FK-506. Neuroimmunophilin activities have not been reported for these compounds, but are anticipated.

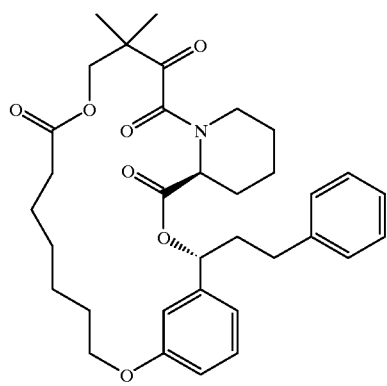

2

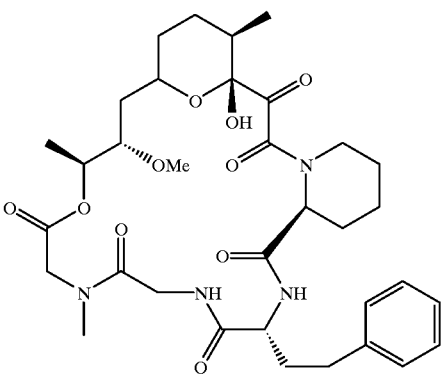

3

In a primate MPTP model of Parkinson's disease, administration of FKBP ligand GPI-1046 caused brain cells to regenerate and behavioral measures to improve. MUTT is a neurotoxin, which when administered to animals, selectively damages nigral-striatal dopamine neurons in the brain, mimicking the damage caused by Parkinson's disease. Whereas before treatment animals were unable to use affected limbs, the FKBP ligand restored the ability of animals to feed themselves and gave improvements in measures of locomotor activity, neurological outcome, and fine motor control. There were also apparent corresponding increases in regrowth of damaged nerve terminals. These results demonstrate the utility of FKBP ligands for treatment of diseases of the CNS.

From the above description, two general approaches towards the design of non-immunosuppressant, neuroimmunophilin ligands can be seen. The first involves the construction of constrained cyclic analogs of FK-506 in which the FKBP binding domain is fixed in a conformation optimal for binding to FKBP. The advantages of this approach are that the conformation of the analogs can be accurately modeled and predicted by computational methods, and the analogs closely resemble parent molecules which have proven pharmacological properties. A disadvantage is that the difficult chemistry limits the numbers and types of compounds that can be prepared. The second approach involves the trial and error construction of acyclic analogs of the FKBP binding domain by conventional medicinal chemistry. The advantages to this approach are that the chemistry is suitable for production of the numerous compounds needed for such interactive chemistry-bioassay approaches. The disadvantages are that the molecular types of compounds that have emerged have no known history of appropriate pharmacological properties, have rather labile ester functional groups, and are too mobile conformationally to predict accurately conformations by computational methods.

The present invention provides useful methods and reagents for both approaches, in that the invention can be used to make polyketides that have the desired activity (whether immunosuppressive or neuroimmunophilin) or can be modified to have the desired activity by chemical means. In one aspect, the invention can be used to produce compounds that optimally bind to FKBP but do not bind to the effector proteins. Specifically, the methods and reagents of the invention can be used to prepare numerous constrained cyclic analogs of FK-520 in which the FKBP binding domain is fixed in a conformation optimal for binding to FKBP. Such compounds will show neuroimmunophilin but not immunosuppressive effects. The invention allows direct manipulation of FK-520 and related chemical structures via genetic engineering of the enzymes involved in the biosynthesis of FK-520 (as well as related compounds, such as FK-506 and rapamycin); similar chemical modifications are simply not possible because of the complexity of the structures. The invention can also be used to introduce "chemical handles" into normally inert positions that permit chemical modifications.

Several general approaches to achieve the development of novel neuroimmunophilin ligands are facilitated by the methods and reagents of the present invention. One approach is to make "point mutations" of the functional groups of the parent FK-520 structure which binds to the effector molecules to eliminate their binding potential. These types of structural modifications are difficult to perform by chemical modification, but can be readily introduced using the invention.

A second, more extensive approach facilitated by the present invention is to utilize molecular modeling to predict optimal structures ab initio that bind to FKBP but not effector molecules. Using the available X-ray crystal structure of FK-520 (or FK-506) bound to FKBP, molecular modeling can be used to predict polyketides that should optimally bind to FKBP but not calcineurin. Various macrolide structures can be generated by linking the ends of the FKBP-binding domain with "all possible" polyketide chains of variable length and substitution patterns that are possible to prepare by genetic manipulation of the FK-520 PKS gene cluster in accordance with the methods of the invention. The ground state conformations of the virtual library will be determined, and those compounds that possess binding domains most likely to bind well to FKBP can be prepared and tested.

Once a compound is identified in accordance with the above approaches, the invention can be used to generate a focused library of analogs around the lead candidate, to "fine tune" the compound for optimal properties. Finally, the genetic engineering methods of the invention can be directed towards producing "chemical handles" that enable medicinal chemists to modify positions of the molecule previously inert to chemical modification. This opens the path to previously prohibited chemical optimization of lead compound by time-proven approaches.

In addition to providing methods for making novel FK-520 analogs and derivatives, the invention also provides reagents and methods for producing unmodified or naturally occurring FK-520 in recombinant host cells of any origin. To obtain these reagents, genomic DNA was isolated from an FK-520-producing strain of *Streptomyces hygroscopicus*, partially digested with restriction enzyme SauIIIA1, and cloned into a cosmid vector to produce a genomic library. This library was then probed with a radioactively-labeled probe generated from *S. hygroscopicus* DNA using PCR and primers complementary to consensus sequences for a KS-encoding region of a modular PKS gene. This probing identified 78 different cosmids, all of which were shown by restriction enzyme mapping to comprise insert DNA derived from the same general location of the chromosomal DNA.

To obtain an independent probe for FK-520 PKS-encoding DNA, a probe was prepared from genomic DNA from an FK-506-producing organism. Motamedi et al., September 1996, *J. Bacteriology* 178(17): 5243–5248, reports the sequence of the MT gene involved in the biosynthesis of FK-506. A probe cotaining FK-506 MT-encoding DNA was generated by PCR and used to probe a genomic library of *S. hygroscopicus* DNA. One cosmid was identified and designated cosmid 34–183. Cosmid 34–183 was digested with restriction enzyme AatII and self-ligated to yield cosmid 34–183A. Cosmid 34–183 was digested with restriction enzyme MluI and self-ligated to yield cosmid 34–183M. Cosmids 34–183A and 34–183M respectively comprise either end of the insert DNA in cosmid 34–183 and thus are useful as probes to identify cosmids that contain additional contiguous DNA.

When used as a probe of the 78 cosmids identified by KS probing technique, cosmid 34–183A identified cosmids 34–122 and 34–123; cosmid 34–183M identified cosmids 34–119, 34126, and 34–156. Restriction enzyme mapping with restriction enzymes EcoRV, EcoRI, and SacI enabled the preparation of maps of the various cosmids and facilitated the construction of a number of subclones for sequencing and further analysis. The restriction site maps for these cosmids and subclones of the invention are shown in FIG. 1.

Further analysis of these cosmids and subclones facilitated the identification of the location of various PKS ORFs, modules in those ORFs, and coding sequences for modification enzymes. Thus, based on the unique sequence for module 14 of the rapamycin PKS and module 10 of the 25 FK-506 PKS, degenerate primers were prepared and used to amplify homologous sequences in the FK-520 PKS gene cluster sequences in the cosmids of the invention. The results showed that cosmids 34–183, 34–119, 34–156, and 34–123 contained such homologous DNA. Similar analyses using degenerate primers corresponding to rapP and P450 gene sequences identified the location of homologues of these genes in the various cosmids and subclones of the invention. The location of these genes and modules is shown on FIG. 1.

FIG. 1 shows that the complete PKS gene cluster of the invention is contained within the insert DNA of cosmids 34–183 (insert size of ~36.1 kb) and 34–126 (insert size of ~29 kb). The P450 oxidase gene is contained within the insert of cosmid 34–122 (insert size of ~34.8 kb). Each of these cosmids has been deposited with the American Type Culture Collection in accordance with the terms of the Budapest Treaty (cosmid 34–183 is available under accession no. ATCC 20335;cosmid 34–126 is available under accession no. ATCC 20336; cosmid 34–122 is available under accession no. ATCC 20337). Various additional reagents of the invention can therefore be isolated from these cosmids. DNA sequence analysis was also performed on the various subclones of the invention, as described in Example 1 and in the sequence listing attached hereto. Based on the disclosure of this nucleotide sequence information as well as the known genetic code, the present invention provides a wide variety of useful compounds for constructing recombinant FK-520 PKS gene clusters, ORFs, modules, domains within modules, and modification enzymes.

Thus, the invention provides DNA molecules in isolated (i.e., not pure, but existing in a preparation in an abundance not found in nature) and purified (i.e., substantially free of contaminating materials or substantially free of materials with which the corresponding DNA would be found in nature) form. These DNA molecules comprise one or more sequences that encode one or more domains (or fragments of such domains) of one or more modules in one or more of the ORFs of the FK-520 PKS gene cluster. Examples of such domains include the KS, AT, DH, KR, EH, ACP, and TE-corresponding (i.e., picolate acid incorporating) domains of at least one of the ten modules of the five ORFs of the gene cluster. In an especially preferred embodiment, the DNA molecule is a recombinant DNA expression vector or plasmid. Such vectors can either replicate in the cytoplasm of the host cell or integrate into the chromosomal DNA of the host cell. In either case, the vector can be a stable vector (i.e., the vector remains present over many cell divisions, even if only with selective pressure) or a transient vector (i.e., the vector is gradually lost by host cells with increasing numbers of cell divisions).

Thus, the various PKS-encoding nucleic acids of the invention can be cloned into one or more recombinant vectors individually or in combination with other nucleic acids. Each activity-encoding nucleic acid can be inserted into the vector with its own separate control elements, or multiple activity-encoding segments can be under the control of a single promoter in the vector. The PKS component nucleic acids of the invention therefore often include flanking restriction sites to allow for facile deletion, insertion, or other manipulation to assist in the construction of expression vectors. The implementation of restriction sites to facilitate vector construction is known to those of skill in the art and can be accomplished using the commonly known techniques, including those described below, such as site-directed mutagenesis and PCR.

The recombinant vectors of the invention will typically include suitable control sequences, or promoters, which include those which function in eucaryotic or procaryotic host cells. Preferred hosts cells for purposes of promoter selection for practice of the present invention include fungal cells, such as procaryotic cells, including Streptomyces cells, and eukaryotic cells, such as yeast and mammalian cells. Suitable control sequences for such cells are well known in the art. Control systems for expression in yeast, including control systems that include not only promoters but also enhancers, translation control sequences, such as ribosome-binding sites, and optionally sequences that direct of secretion are widely available and routinely used. Particularly useful promoters for procaryotic hosts include those from PKS gene clusters that result in the production of polyketides as secondary metabolites, including those from aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from genes that encode biosynthetic enzymes such as for tryptophan (trp) or beta-lactamase (bla), and bacteriophage promoters, such as the lambda PL and T5 promoters. In addition, synthetic promoters, such as the tac promoter (U.S. Pat. No. 4,551,433), can be used.

Particularly useful promoters and control systems are those that activate transcription of ORFs and accordingly translation of the mRNA and expression of protein during transition of the host cell from growth to stationary phase (as occurs, for Streptomyces, in the vegetative mycelium). The control system contained in the plasmid identified as pCK7, i.e., the actI/actIII promoter pair and the actII-ORF4 gene (an activator gene), is particularly preferred. See U.S. Pat. Nos. 5,672,491 and 5,712,146, each of which is incorporated herein by reference. Generally, it may sometimes be desirable to allow for regulation of expression of the PKS gene cluster relative to the stage of growth of the host cell. Illustrative regulatory control sequences are known to those of skill in the art; examples include promoters that cause the expression of a gene to be turned on or off in response to a chemical or physical stimulus, including the presence of a specific compound.

Selectable markers can also be included in the recombinant expression vectors of the invention. A variety of selectable markers are known which are useful in selecting for transformed cell lines and generally comprise a gene whose expression confers a selectable phenotype on transformed cells when the cells are grown in an appropriate selective medium. Such markers include, for example, genes which confer antibiotic resistance, i.e., the tsr gene, or sensitivity to the plasmid. Alternatively, several polyketides are naturally colored and this characteristic provides an alternative marker for screening cells successfully transformed with certain vectors of the invention.

Methods for introducing the recombinant vectors of the present invention into suitable hosts are known to those of skill in the art and typically include the use of $CaCl_2$ or other agents, such as divalent cations, lipofection, DMSO, protoplast transformation and electroporation.

Particularly preferred host cells for certain applications of the present invention are those that do not otherwise (i.e., in the absence of transformation with a vector of the invention) produce a polyketide. Choice of such a host cell makes easier the determination that transformation has occurred as well as purification of the polyketide produced. Illustrative host cells of this type include the modified S. coelicolor CH999 host cell and other host cells described in U.S. Pat. Nos. 5,712,416 and 5,672,491, each of which is incorporated herein by reference. Other host cells that can be utilized for purposes of the present invention include E. coli, mammalian, Myxobacteria, Saccharomyces, Saccharopolyspora, Streptomyces, yeast, and plant cells; see, e.g., PCT patent publication No. WO 98/27203 and U.S. patent application Ser. No. 09/114,083, filed Jul. 10, 1998, inventor Mary Betlach, both of which are incorporated herein by reference.

The recombinant DNA vectors and host cells of the invention can be used not only to produce FK-520 but also to produce other polyketide and polyketide-related compounds. In one aspect, the invention provides nucleic acids that encode a mutated form of a naturally-occurring PKS domain, module, ORF, and gene cluster, and so can be used to prepare an FK-520-related compound.

Mutations can be introduced to the nucleic acid compounds of the invention using conventional techniques. The substrates for mutation can be an entire PKS gene cluster, ORF, module, or domain. Techniques for introducing mutations include preparing synthetic oligonucleotides including the mutations and inserting the mutated sequence into the appropriate vector using restriction endonuclease digestion. See, e.g., Kunkel, 1985, *Proc Natl Acad Sci USA* 82:448; Geisselsoder et al., 1987, *BioTechniques* 5:786. Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by regulating primer length and base composition and by keeping the mutant base centrally located. See Zoller and Smith, 1983, *Methods in Enzymology* 100:468. Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations. See, e.g., Dalbie-McFarland et al., 1982, *Proc Natl Acad Sci USA* 79:6409. One can also use PCR mutagenesis to effect the desired mutations. See U.S. Pat. No. 5,605,793.

Random mutagenesis of selected portions of nucleic acids encoding enzymatic activities can be accomplished by several different techniques. These techniques include inserting an oligonucleotide linker randomly into a plasmid, irradiating with X-rays or ultraviolet light, incorporating nucleotides during in vitro DNA synthesis, performing error-prone PCR mutagenesis, preparing synthetic mutants, and treating plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In another embodiment, the invention provides polyketides other than FK-520 by providing expression vectors that encode a chimeric PKS. The chimeric PKSs of the invention can be conceptually viewed as those substantially patterned on either the FK-520 PKS or a non-FK-520 PKS. In either case, the chimera includes one or more functional domains of the FK-520 PKS or a mutated version of such a domain. The invention also provides recombinant DNA vectors and host cells containing those vectors in which the chimeric PKS is produced together with one or more polyketide modification enzymes. Such enzymes can include, for example, a TE or its picolate-acid incorporating homologue, a rapP homologue, an MT, one or more sugar biosynthetic enzymes or transferases, a hydroxylase, or a P450 oxidase homologue.

With respect to chimeric PKS gene clusters, ORFs, and modules, preferred examples include construction of chimeric PKS enzymes wherein the erythromycin, FK-506, FK-520, narbomycin, oleandomycin, picromycin, rapamycin, spiramycin, or tylosin PKS gene clusters function as accepting scaffolds or ORF, module, or domain donors. In this regard, the examples of FK-506 PKS and rapamycin PKS are preferred for constructing chimeric PKS gene clusters for production of polyketides with neuroimmunophilin activity.

Those of skill in the art will recognize that it is not necessary to replace an entire domain, module, or ORF of the target (scaffold) PKS with a corresponding segment of the PKS of the invention, rather peptide subsequences of a PKS domain segement that correspond to a peptide subsequence in the scaffold PKS, or which otherwise provide useful function, can be used. In this context, the term "scaffold" defines the target PKS encoding DNA having one or more domain fragments, domains, modules, or ORFs that are being replaced, for example by a corresponding FK-520 PKS gene cluster segments. Accordingly, appropriate nucleic acids, typically DNA, for construction of such chimeric PKS include those that encode at least 10, 15, 20, or more amino acids of a selected FK-520 PKS segment. Of course, portions of, or all of, the desired coding sequences can be synthesized using standard solid phase synthesis methods, such as those described by Jaye et al., 1984, *J Biol Chem* 259:6331, and which are available commercially from, for example, Applied Biosystems, Inc.

Thus, the invention provides recombinant materials for the production of PKS genes or gene clusters, as well as "combinatorial" libraries of PKS expression vectors and the corresponding polyketides, wherein the term "combinatorial" reflects that the library encompasses a variety of different PKS gene clusters and corresponding polyketides. Of course, the methods of the invention may also be directed to the preparation of a single polyketide. The resulting polyketides may be further modified to convert them to compounds useful for a particular purposes, such as an antibiotic, an immunosuppressant, or a neuroimmunophilin, for example.

Thus, in another aspect, the invention is directed to a multiplicity, or a library, of cells comprising, PKS genes wherein each different cell of the library contains an expression vector for the production of a different modular PKS. In a preferred embodiment, the different PKS are derived from the PKS of the invention. In another preferred embodiment, the library of different modular PKS is obtained by modifying one or more domains or modules of a PKS ORF or gene cluster. The invention also provides methods to produce libraries of PKS complexes and libraries of polyketides by culturing these cells or by the use of cell-free extracts. See U.S. patent application Ser. No. 08/896,323, filed Jul. 17, 1997 and PCT patent publication No. 97/02358, each of which is incorporated herein by reference.

Each individual and unique colony in a library of the invention has the ability to produce a particular PKS synthase and ultimately a particular polyketide. Typically, there will be duplications in the colonies; the subset of the transformed colonies that contains a different PKS in each member colony can be considered the library. Alternatively, the expression vectors can be used individually to transform hosts, which transformed hosts are then assembled into a library. The number of different polyketides that are produced by the library is typically at least four, more typically at least ten, preferably at least 20, more preferably at least 50 or more, reflecting similar numbers of different altered PKS gene clusters and PKS gene products. The number of members in a library of the invention can be determined by the applications of the practitioner; the degrees of freedom with respect to the variation of starter and extender units, stereochemistry, oxidation state, and chain length is quite large and so enables the construction of very large libraries.

Colonies in the libraries of the invention produce the relevant PKS enzymes and can produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand or exposure to a cell. Binding can be detected either directly or through a competition assay. Means to screen such libraries for binding are well known in the art. Alternatively, individual polyketide members of the library can be tested against a desired target. In this event, screens wherein the biological response of the target is measured are preferred.

Those of skill in the art will recognize that, in providing libraries of PKS gene clusters, the invention also provides each individual PKS gene cluster in the library. In one embodiment, these members each comprise a polyketide synthase gene cluster derived from a naturally occurring PKS. In another embodiment, each member contains at least two functional PKS modules, and one or both of these modules contains mutations, deletions, or replacements of one or more of the activities of the naturally occurring module. In another embodiment, each member produces a polyketide not found in nature.

Particularly preferred embodiments of the invention include those recombinant PKS enzymes and PKS modules, ORFs, and gene clusters in which a KS, AT, ACP, KR, DH or ER has been either deleted or deleted and replaced. If replaced, the activity or domain can be replaced by a version of the activity from a different PKS or from another module within the same PKS gene cluster. Also preferred are derivatives where at least one non-condensation cycle enzymatic activity (KR, DH or ER) has been deleted or wherein any of these activities has been mutated so as to change the polyketide produced from the PKS. In another embodiment, the domain or module of one PKS, such as from erythromycin, FK- 506, or rapamycin, is replaced with that of a FK-520 PKS domain or module. Such methods are applicable also to fragments of domains, such as those encoding an active site.

In constructing a recombinant chimeric PKS module, ORF, or gene cluster of the invention, a variety of embodiments are provided. In one embodiment, one can select the polyketide chain length by selecting the appropriate number of modules in the PKS gene cluster. In another, one can determine the nature of the carbon skeleton of the polyketide by selecting the specificities of the acyl transferases that determine the nature of the extender units at each position—e.g., malonyl, methyl malonyl, ethyl malonyl, and the like. In another, one can select the appropriate loading domain specificity to effect the desired carbon skeleton of the polyketide. In another, one can select the oxidation state at various positions of the polyketide by selecting the appropriate, if any, dehydratase and reductase domains of the modules to determine the presence and location of ketone, alcohol, alkene or alkane substituents at particular locations in the polyketide. In yet another embodiment, one can select the stereochemistry of the resulting polyketide by selecting the AT/KS specificity (as when there is no reductive cycle or the reductive cycles consists of only a ketoreductase); by selecting the ketoreductase to determine the chirality of any alcohol; and by selecting the enoyl reductase specificity.

Thus, the invention provides methods for constructing PKS modules, ORFs, and gene clusters by deleting or inactivating domains or modules, inserting domains or modules the same or different PKS systems, or by otherwise mutating such compounds using standard procedures for obtaining genetic alterations. Thus, to obtain nucleic acids encoding a variety of derivatives of a PKS gene cluster, and thus a variety of polyketides, as in the construction of a library, a desired number of constructs can be obtained by "mixing and matching" PKS domains, modules, and ORFs. If replacement of a particular target region in a host PKS gene cluster, ORF, or module is to be made, this replacement can be conducted in vitro using suitable restriction enzymes. This replacement can be effected in vivo using recombinant techniques involving homologous segments of nucleic acid framing the replacement gene in a donor plasmid and a receptor region in a recipient plasmid. Such systems, advantageously involving plasmids of differing temperature sensitivities are described, for example, in U.S. Pat. Nos. 5,712,416 and 5,672,491, incorporated herein by reference.

Thus, the invention provides useful reagents and methods for the production of polyketides. In one aspect, the invention provides recombinant vectors encoding the complete PKS gene cluster and associated modification enzymes for the polyketide FK-520. In another aspect, the invention provides nucleic acids that encode the various domains, including the KS, AT, ACP, KR, DH, ER, and picolate-incorporating activity domains of all ten modules of the FK-520 gene cluster. In another aspect, the invention provides nucleic acids that encode the modification enzymes that encode the activities that modify the FK- 520 polyketide. In another aspect, the invention provides mutated versions of the foregoing that differ from their unmutated counterparts in activity or specificity. In another aspect, the invention provides chimeric PKS modules, ORFs, and gene clusters comprising one or more domains of the PKS PKS of the invention (or a mutant form thereof) and one or more domains of a non-FK-520 PKS. Further, the invention provides host cells comprising such vectors, methods of culturing host cells to produce the recombinant PKS of the invention as well as the polyketides produced by those PKS, and a variety of novel polyketides.

EXAMPLES

To facilitate the construction of the nucleic acids of the invention, various cosmids of the invention were digested with restriction enzymes, and the resulting fragments of the original insert DNA were subcloned and the subclones sequenced. The sequences generated were sequences from either end of the insert DNA in the subclone. The various subclones that were made are identified in FIG. 1. Below, the various sequences obtained from these subclones are shown, together with the amino acid sequence of the polypeptide encoded by the DNA sequence. In each case, the DNA sequence is identified with an alphanumeric designation that includes, in order, the numeric designation of the cosmid from which the subclone was derived (i.e., 34–183 for cosmid 34–183), the name of the subclone, and the generic primer (i.e., "T7" or "T3") used to generate the sequence. The sequence information for each of the inserts in each of the subclones is not complete, but the sequence information provided is helpul in locating various coding sequences of interest in the cosmids and vectors of the invention.

The first sequence is PKS-derived coding sequence designated 34–183R1AS1.T7 or SEQ.ID.NO:1.
G A A G A A C T C C G C G T C G A A G T C T C C G-
GCGCCGTTCACGAAGCCGCCCTCG CGGACGTAC-
G A G G T A C C G G G G T G G T C G G G G T C-
C G G G T G G T A C A G G G C G T
C C A T G T C C C A G C C C C G G T C G G T G G G-
GAACGCGGTCATCCCGTCACGGCC CTCGGCCAC-
C A G C C G C C A C A G G T C T T C G G G C G A C T C-
C A C A T C G C C C G G G
A G G C G G C A G G C C A T C G C C A C G A T C G C-
GATGGGGTCATCATCGGCGACGG CCACCGCCGTG-
G C C T C G G T G A C G T C C T C C G C A C C G A G-

CAACTCGGCGCG
CAGGTGCTGGGCCAGCGCGTTCGGC-
GAGGGGTGGTCGAAGACGAGGGTG GCGGGCAGC-
CGCAGCCCGGTGGCGGCGTTCAGCCGGT-
TGCGGAGTTCCA
CGGCCGTGAGCGAGTCGAAGCCAGCTC-
CTTGAACGCCTTCGTCGCGTTCA CGGCTTCCTGC-
GAGGTGTGCCGAGCACGGCGGCACGTCG-
GCGCGTACAG
GTCCAGCAGGATGCGCGGCTCGCTCG-
GACGCGGCGGCAGCGGCGTGCAG CGCGAGCCCG-
GCGCCGTGCGTACGACGCGCGACGCGCG-
GACGTGGCGTA
CAGCCCTGAACGCGCGGAGCCACCGTCT-
GCGACGCCGGCAGTCAGTGAG GGACCGACCGTGT-
TCGGCAGCCGCTGACGGTCAACGTCAT-
CAATGCATGT
GGACATCGCCGCTATCGGCGATTCGCT-
TCAAGTCGGATCAGTACTCGTCA GGCAGAAGAG
The above sequence comprises an ORF that encodes a
protein with the amino acid sequence shown below,
SEQ.ID.NO:2:
EELRVEVSGAVHEAALADVRGTGV-
VGVRVVQGVHVPAPVGGERGHPVTAL GHQPPQVF-
GRLHIAREAAGHRHDRDGVIIGDGHR-
RGLGDVLRTEQLGAQVL
GQRVRRGVVEDEGGGQPQPGGGVQP-
VAEFHGRERVEASSLNAFVAFTASCE VCRARRHV-
GAYRSSRMRGSLGRGGSGVQREPGAVRT-
TRDARTWRTALNARS
HRLRRRQSVRDRPCSAAADGQRHQCM-
WTSPLSAIRFKSDQYSSGRR The second sequence is PKS-derived coding sequence
designated 34–183R1AS2.T7 or SEQ.ID.NO:3.
GGCGGGCGCCGTGGCCGACCGG-
GACTCTCCACCGAACACGTCGACGCCG TGGACGC-
CCATGGAACGGGGACCCCGCTCGGTGAC-
CCCATCGAGGCCCA
GGCGCTGCTGGCCACCTACGGCCGGGAC-
CGGGCGGCGGACCGGCCCCTG
TGGCTGGGCTCGCTGAAGTCGAA-
CATCGGGCATACGCAGGCGGCGGCCG GTGTCG-
GCGGTGTCATCAAGATGGTGATGGCGAT-
GCGGCACGGTGTGCTG
CCGAAGACGTTGCATGTGGAGGAGC-
CGACGCCGCATGTGGACTGGTCGT CGGGTGCG-
GTCTCGCTGCTGACGGAGGCGCGG-
GAGTGGCCGGAGACGGA
CGGCCGGCCGCGCCGGGCGGCCGT-
GTCGTCCTTCGGCATCAGCGGCACC AACGC-
CCACGTCATCCTCGAACAGCCGCCG-
GCTCCGGCCGACGAACAGC
CGATGGTGAGCCGGGTCCCGGCCCAGC-
CACCGCGCTGCCTGGGTGATCTC CGGCGGGAGT-
GCCGATGCCTGCGCGAACAGGCCGCCG-
GCTGGCGTCGTC
CTCGACGAGGTGGAGTGCGAGAGACG-
GACCTGAAGAGGCGGACGGCAC CGGCATCGT-
GCGCGTCACCCCGCTGACCTCGCGTAT-
TCGCTCGCCAACTT T
The above sequence comprises an ORF that encodes a
protein with the amino acid sequence shown below,
SEQ.ID.NO:4:
GGRRGRPGLSTEHVDAVDAHGTGTPLGD-
PIEAQALLATYGRDRAADRPLWL GSLKSNIGHT-
QAAAGVGGVIKMVMGVLPKTLHVEEPT-
PHVDWSSGA
VSLLTEAREWPETDGRPRRAAVSSFGIS-
GTNAHVILEQPPAPADEQPMVSRVP AQPPRCLGDLR-
RECRCLREQAAGWRRPRRGGVRET
DLKRRTAPASCASPR*P RVFARQL The third sequence is PKS-derived coding sequence des-
ignated 34–183R1A.T7 or SEQ.ID.NO:5.
CCAGGCCGGGTTCCTGGACCGGCTTG-
GACCGCGTTGACGCGCGGGGAGC CGTCGCCTCTG-
GTTGTCGAGGGCGTGGCGACGACGGGTC-
CGGTGGCCTTT
CTCTTCGACGGGTCACGGGGTACG-
CAGCGGGTGGGGATGGGGCGTGAGC TGTAT-
GAGTCGTATCCGGTGTrCGCGGAGGCGT-
TCGACGCGGTGTGTGAG
GGGTTCGCGCCGCTGCCGGTGAAG-
GACGTGGTGTTCGGG
The above sequence comprises an ORF that encodes a
protein with the amino acid sequence shown below,
SEQ.ID.NO:6:
PGRVPGPAWTALTRGEPSPLVVEGVATF-
GPVAFLFDGSRGTQRVGMGRELYE SYPVFAEAF-
DAVCEGFAPLPVKDVVFG The fourth sequence is PKS-derived coding sequence
designated 34–183RVA.T3 or SEQ.ID.NO:7.
GATATCACCGTGGCGTGCGGGCCGT-
TGACGGCCGCGATGGCGACCCGGT CGATGGC-
GATCTGGTCCATGGCGACCTGGTCA-
GAGCCGGTCAGCGACGC
GCGCACCTCGGCCTCGCCGGCCCGCAC-
CGACACCATCGCCCCGCCCGGC GGCAGCGCCTG-
CATCAGCCGCCCGCGCGCCGCGACGAGC-
CGGCAGGCGT
CGGGGAGGGAGAGGACGCCGGAGA-
CATGGGCGGCCGCGAGTTCGCCGA CCGAATGC-
CCCAGCAGATAGTCGGGGCGCAC-
CCCCCAGGACTCCAGCAA
CCGGAACAGCGCCACCTCGACGGCGAA-
CAGGGCGGGCTGCGCGTACTCG GTACGGTCCAG-
CAGCTCCTGGTCGGCGCCGAACAC-
CACGTCCTTCAGCG
GCCGCTCCAGCTCCAGCCGCTCGCAGAC-
CGCGTCGAACGCCTCGGCGAA CACCGGG-
TACGTCGCGTACAGCTCACGCCCATGC-
CGCCGCGTGGGGCCC
CTGACAGGGAAGAGGAGGCGCACTCGC-
CTCCACGACCGTGCCCGTCACG GTGTTCGGTTCG-
GCTCGCCCGCCGCGAGGTGTTCAGCGC-
CGCCCGAAACC
CCTCTCGTTCGTCGCGAGAGCACG-
GCGCGCTCAGCCCGGCCGAATGTGTG GCAGCG-
CACGCCGATGTCGGGCGGGCGGGTC-
CTCGGGTGGTCGTCAAGT
TACGGGCGCAGCCGCTTCGC-
CGTGGGCGGGAGGGCCTGTTCGTCTTGGCG CAC-
GAATCAGGGCCGCGCGTTGGACG-
TACGTGGGCTGGTGGGCATGGTC
CTGGGCGTTTGGCAGGCGGG
The above sequence comprises an ORF that encodes a
protein with the amino acid sequence shown below,
SEQ.ID.NO:8:
PACQTPRTMPTSPRTSNARP*FVRQDEQALPPTAKRL
RP*LDDHPRTRPPDIGV RCHTFGRAERAVLSR-
RTRGVSGGAEHLAAGEPNRT
P*RARSWRRVRLLFPVR GPTRRHGRELYATYPVFAE-
AFDAVCERLELERPLKDVVFGADQELLDRTEYA
QPALFAVEVALFRLLESWGVRP-
DYLLGHSVGELAAAHVSGVLSLPDACRLVA ARGR-
LMQALPPGGAMVSVRAGEAEVRASLTGS-
DQVAMDQIAIDRVAIAAVN GPHATVI The fifth sequence is PKS-derived coding sequence designated 34–183RVA.T7 or SEQ.ID.NO:9.
GGCTTTTCCCTGGCGACGACGAGGGACTCCTTCCCCCACCGCGCCGTGGT GACCGCACATGACCAGGCCGGGTTCCTGGACGGCTTGGACGCGTTGACG
CGCGGGGAGCCGTCGCCTCTGGTTGTCGAGGGCGTGGCGACGACGGGTC CGGTGGCCTTTCTCTTCGCGGGTCAGGGGTCGCAGCGGGTGGGGATGGGG
CGTGAGCTGTATGAGTCGTATCCGGTGTTCGCGGAGGCGTTCGACGCGGT GTGTGAGGGGTCGCGCCGCTGCCGGTGAAGGACGTGGTGTTCGGAGCT
GACCAGGAGCTGCTGGATCGTACGGAGTTCGCTCAGCCTGCGCTGTTT The above sequence comprises an ORF that encodes a protein with the amino acid sequence shown below, SEQ.ID.NO:10:
GFSLATTRDSFPHRAVVTAHDQAGFLDGLDALTRGEPSPLVVEGVATTGPVA FLFAGQGSQRVGMGRELYESYPVFAEAFDAVCEGFAPLPVKDVVFGADQELL DRTEFAQPALF The sixth sequence is PKS-derived coding sequence designated 34–183RVB.T3 or SEQ.ID.NO:11.
GATATCTCCACCATCCAATGGGCCAGCACCGGCTATCTGCTGGCCCTGTC GGCGGTCATCCCGCTCACCGGCTGGGCCGTGGAACGCTTCGGCGCCCGG
ACGATGTGGCTGTTCTCGCTGACCGCCTTCCTGGCCGGGTCCGCGCTCTGC GGCGCCGCGTGGTCGGTCGGCAGCCTGATCGCCTTCCGGGTCCTCCAGGG
CATCGGCGGCGGCCTGATCACCCCGGTGATGCAGACCATCCTGGTCCGC GCGGCCGGTCCGCGGCGGATCGGCCGCATCATGAGCATCGTGGCGGTGC
CCGGCCATCTCTCCCCGATCGTCGGTCCGTTGGTCGGCGGCGCCATCATC GACTCCGTCAGCTGGCGCTGGATCTTCTACGTCAACGTGCCCATCTGTGT
GATCGCCCTGCTGCTGGCCTGGCGGGGTGTCCCCGCGACACCAGGAGC GACACCGCCGCCCGGCTGGACGTGCTCGGACTGTCGCTGCTGTCCCCGGG
CTCGCGGCGATCATCTACGGGGCTGTCGCAGACAGCAGGCCGAGGGTTC GGGCGACCCGGTCGTGTCTCCTGTCGCTGGGCGCGTCTGCTGGCGCCTCG
CGGCCAGCGCTGCGCACCCGATCACCCGTCTGAACTGCGCTGTTCGGCAC GCCTCGTCACGCCGGCACGTGCTGATGTTCTGGGGCGCATGTTCGTCTTC
GGGCGAATGCTGCTGATGCCGCCTACCTACCGACGGTCCGAACAGACCG CCTGG The above sequence comprises an ORF that encodes a protein with the amino acid sequence shown below, SEQ.ID.NO:12:
IPVALDNEPFGSRFPQQIGVLQSRVEAMLEERLETVHGITVERGRELIGFEQDE HGVTATVRGPEGRETLLRGRYLVGCDGSRSRVRRVLGLPFDGTDGGPQTRVA ADVVLVRPPEKWFDGQAPQGVGEVDGRDVRMLPDVGLTGMITLSEGC The seventh sequence is PKS-derived coding sequence designated 34–119.1.T7 or SEQ.ID.NO:13.
GACACCCCGTCGCCGCCGGTGGCCACCAGGTCCCACAGACCCTCGGGAG ACTCCACCCCGCCCGGGAAACGGCACGCCATCCCCACGATCGCCAACGG
CTCATCACTCGCCGCCACCGCACCCGGCGGCAACGCCGCCACGGCATCC GCCTCCCCGCCGAAGAGCTCCGCACCCAGCCGGCCCGCCAGCGCCGCGG
GCGTCGGGTAGTCGAACACCAGCGTCGCCGGAAGCCTCAGGCCCGTTGC CGTATCCAGCCGGTTCCGCAGTTCGACGGCGGTCAGCGAGTCGAAGCCG
ATCTCCCGGAACGCCTTGTCGGCGTCCACGGCCGCCTCGGAGCCGTGGCC GAGCGCGATCGCGGCCTCGTGCCGCACCAGCTCCACGAGGTGTGCGGCC
CGCTCCTCCGGCCGAGTCCGGCCAGGCGCTCGCGGAGCGAGCGGGTCGC GGCGCTGCGCGCGGGCGCGCACGGTCGTACGAGCCGAGACAGCGGGGA
GTCGCGCTGGTCGCGCAGACGCCTGTCAGCGCATGGCAGCAGAACGGTG TGCGAGCGACGCGCACGATCCC The above sequence comprises an ORF that encodes a protein with the amino acid sequence shown below, SEQ.ID.NO:14:
GSCASLAHRSAAMR*QASARPARLPAVSARTTVRAR AQRRDPLAPRAPGRTR PEERAAHLVELVRHEAAIALGHGSEAAVDADKAFREIGFDSLTAVELRNRLD TATGLRLPATLVFDYPTPAALAGRLGAELFGGEADAVAALPPGAVAASDEPL AIVGMACRFPGGVESPEGLWDLVATGGDGV The eighth sequence is PKS-derived coding sequence designated 34–119M or SEQ.ID.NO:15.
TATCGAAGTGGCGTTGTTCCGGTTGGTGAGTCCTGGGGTGTGGTCCCGGA TTTTGTGCTGGGGCATTCGGTGGGTGAGTTGGCTGCCGCGCATGTGGCGG
GGGTGTTTCGCTGGGGGACGC The above sequence comprises an ORF that encodes a protein with the amino acid sequence shown below, SEQ.ID.NO:16:
YRSGVVPVGESWGVVPDFVLGHSVGELAAAHVAGVFSLGD The ninth sequence is PKSderived coding sequence designated 34–183RVB.T7 or SEQ.ID.NO:17.
CGGGCGCCGGAGGCGGAGGTCGCCGCTGTCGCCGCGCACTGGGAGGCGG CCGGCCGCCGGGTGAAGCGCCTGCGGGTCAGCCACGCCTTCCACTCGCC
GCTCATGGACGCGATGCTCGAGCCGTTCCGCCAGGTCGCCGAAAGCGTG TCGTACGAGCCCCCGCGGATCGCGATCGTCTCCGACCTGACCGGCCGCGT
CGTCGGCGCGGCCGAGATCGGCACGGCCGACTACTGGGTGCGGCACGTC CGCGAGTGCGTACGGTTCCACGACGGTCTGAGCCGACTGGACGGCCAGG
GCGTCGCCACCTTCCTGGAGCTGGGGCCGGCCGGAGTCCTGTCCGCCATG GGCCAGGAGTCCGTCTCCGCGTTCTGTGCGCTGATTCCGCTGCTGCGCGA
GGGCCGCCCGAGGCCGACTCCGTGCGCTCGGCGTCGCGCCGGCCATGTG CGGGTGTCGCGTGACTGACGGC The above sequence comprises an ORF that encodes a protein with the amino acid sequence shown below, SEQ.ID.NO:18:
RAPEAEVAAVAAHWEAAGRRVKRLRVSHAFHSPLMDAMLEPFRQVAESVSY EPPRIAIVS- DLTGRVVGAAEIGTADYWVRIVRECVRF-
HDGLSRLDGQGVATFL
ELGPAGVLSAMGQESVSAFCALIPLLREGRPRPTPCA
RRRAGHVRVSRD*R The tenth sequence is coding sequence designated 34–183R1B.T3 or SEQ.ID.NO:19 that has homology to a gene that encodes a mono-oxygenase.
ATTCCGGTGGCCCTCGACAATGAGCCGT-
TCGGCTCCCGGTTCCCGCAGCA GATCGGCGTC-
CTCCAGTCGCGGGTGGAAGCGATGCTC-
GAAGAACGGCTG
GAAACCGTGCACGGAATCACCGTG-
GAGCGCGGCCGGGAACTCATCGGTT TCGAGCAG-
GACGAGCACGGCGTCACGGCCACCGTC-
CGGGGCCCGGAGG
GCCGGGAGACGCTGCTGCGCGGCCGC-
TATCTCGTGGGGTGTGACGGTTCG CGGAG-
CAGGGTGCGCAGGGTGCTGGGCCTGC-
CGTTCGACGGCACGGACG
GCGGCCCGCAGACCCGGGTGGCGGC-
CGATGTGGTGCTGGTGCGGCCGCC CGAGAAGTG-
GTTCGACGGCCAGGCCCCG-
CAAGGGGTCGGCGAGGTGGA
CGGACGCGATGTCCGGATGCTGCCG-
GACGTGGGACTGACCGGGATGATC ACCCTGAGC-
GAGGGCTGC The above sequence comprises an ORF that encodes a protein with the amino acid sequence shown below, SEQ.ID.NO:20:
IPVALDNEPFGSRFPQQIGVLQSRVEAM-
LEERLETVHGITVERGRELIGFEQDE HGVTATVRG-
PEGRETLLRGRYLVGCDGSRSRVRRV-
LGLPFDGTDGGPQTRVA
ADVVLVRPPEKWFDGQAPQGVGEVDGRD-
VRMLPDVGLTGMITLSEGC The eleventh sequence is coding sequence designated 34–183R1B.T7 or SEQ.ID.NO:21.
AATTCGCGGCCGCATAATACGACTCAC-
TATAGGGATCGCCTTCTGCTGCG GCGCCGTGCT-
GCTTCCCGGGGCGCTCCTGGCGGGCT-
GACCGTTACTTCGT
TGCAGAGGAAAGCGATGACCGAGCCAG-
CAGAACCCCAGTACCCGCAGG CCCCGCCACCGAC-
CTACCCACAAGCCCCGCCACCGGCCTACC The above sequence comprises an ORF that encodes a protein with the amino acid sequence shown below, SEQ.ID.NO:22:
NSRPHNTTHYRDRLLLRRRAASRGAPG-
GLTVTSLQRKAMTEPAEPQYPQAPP PTYPQAPPPAY The twelfth sequence is coding sequence designated 34–183RVE.T3 or SEQ.ID.NO:23 that has homology to a gene that encodes a regulatory protein.
GACCGCAGCTGGGGCGTGGCCCTCG-
GCGCGCCGCTGGGCATCCTGCTCC AGGCCATGAC-
CTCCCTGGGACGCCATGCCGAGGCCGAG-
GAACTGACCCG
GGCGGCGCCGCCGGAGCTGTTCCAGAC-
CCGCTGGGGGCTGCTGTACCTGT ACGCCCGGGGC-
CGGTACCACCTGGCGGCCAACCGGCTC-
CAGGCCGGGCT
GAGCGACCTCACCACCTGCGGTGAGCT-
CATGACCGCCTGGGACATGGAC CTGCCGGGCT-
TCATCCCCTGGCGCGCCGACGCCGCGCG-
GATCCATCTGCG
GCTGGGGAACGTACGGCAGGCCCGGCG-
GCTGGCCGAGGAGCAGCTGGC CCGGCCCCTCAC-
CACGGGCTCCCGCACCCATGGCATCGC-
CCTGCGCACG
CTGGCGGCCTGTAGTGAGCTCAAA-
CAGCGGCCCCACCTGCTGCGCAAGG CCGCCGAG-
GAGCTCCAGGAGCATGGCGACCGACTG-
GAGCTGCGGAGAC
CTCACCGATCTCAGCGAGGCCAC-
TACGCGCTGGCGAGTTCGACGGGGCC GGATGATG-
GCGCGCATGGCATGCACGTGGCACGAGT-
GCGTACGGACGCG
CTGCGCAGCGCTGTCGTGTGCTGCT-
GAGAGACTCGAGCGCTGATCGACCC GCGGGG-
TACGGCTGACGATGCGACTGCGGGT-
GTCGGCCTGCCGTCAGGG
ACAGCAGCGGTGATCGCGCCAGCTTAT-
TACGTACGCGGTGACTGCATGA CAGCATGCAGCT-
GACGTACACAGGGTATGCGTTGCTCAC-
TACGGCCAAT ACGGTGG The above sequence comprises an ORF that encodes a protein with the amino acid sequence shown below, SEQ.ID.NO:24:
DRSWGVALGAPLGILLQAMTSLGRHAE-
AEELTRAAPPELFQTRWGLLYLYAR GRYHLAANR-
LQAGLSDLTTCGELMTAWDMDLPGFIP-
WRADAARIHLRLGN
VRQARRLAEEQLARPLTTGSRTHGIAL-
RTLAACSELKQRPHLLRKAAEELQEH GDRLELR-
RPHRSQRGHYALASSTGPDDGAHGMHVA
RVRTDALRSAVVCC*E TRALIDPRGTADDAT-
AGVGLPSGTAAVIAPAYYVRGD
CMTACS*RTQGMRCS LRPIRW The thirteenth sequence is coding sequence designated 34–183R1C.T3 or SEQ.ID.NO:25.
GAATTCCCACGGGACGAGGTGGCCAT-
GACCGTGCAAGCCCCCGAAGCAC CGTTGCGC-
GAACTCACGAATGAGGAGGTGGCCGC-
CTACCGGGAGGACGG
CGCCATACGAGCGTCGGGACTGTTCTC-
CGAGGAGTGGGTGGCCCGGATA ACGGAGGCCGTC-
GACTACGTCCTGGCCAATCCCTCCG-
TACTGGCGCAGG
CGACCGCCGACTTCTCCGAGGGAAAGGC-
GAACGGCGACGCTTTCATGTG GAAGACACATGAG-
GCATTCCGTGATTTCGTCTTCCGCTCAC-
CGGCCTCCC
GGGTCGCCCAGCGGCTCTTCGGCTCACA-
GACCGTCACCGCCTTCTACGAC CAGGTGTTCAC-
CAAGCCGCGGGCACCGCGAAGC-
CCACTCCGTTCCACG
AGGACGCCACGTCCTTCCCCATC-
GACGGGGACCAGGTCTGCGCGATGTG GATCGC-
CCTGGACCACTGCGGTCCCGAAACGGC-
CGCCCTGACCGTCGTC
CGTGGCTCGCACCGCTGGGGAGCGGGAC-
CCGGGCCCGGTCACCTCCAGC CTGATGCAC-
CCGGGCATGCAGGCGGGGCAGAACACAC-
CGAGGCGGGG
ACGCACCCGAGTCGGGGGGCCGAGC-
CGAGTCGGGGGGCGGACCGCCGT CCGAAAC-
CGCGGGACGTGCTCACCTGGGACGAA-
GAGGACCTGCCTCCGC
CTGGGATCTGGCCCCGCAAGCCGGT-
CATTTTCACCCGCCCGCCCTGACGG GTTACCG-
GACCGCCCGGCAGGGCGCGGGCTTGTTC-
CGCTGGCTGGCCAC
GGCTTACCTCAGCCGAGGCTATGCATCGTGGAC The above sequence comprises an ORF that encodes a protein with the amino acid sequence shown below, SEQ.ID.NO:26:
EFPRDEVAMTVQAPEAPLRELTNE-
EVAAYREDGAIRASGLFSEEWVARITEAV DYV- LANPSVLAQATADFSEGKANGDAFMWK-
THEAFRDFVFRSPASRVAQRL
FGSQTVTAFYDQVFTKPRGTAKPTPFHE-
DATSFPIDGDQVCAMWIALDHCGP ETAALTVVRG-
SHRWGAGPGPGHLQPDAPGHAGGAE-
HTRGGDAPESGGRAE
SGGGPPSETAGRAHLGRRGPASAWD-
LAPQAGHFHPPALTGYRTARQGAGLF RWLATAYLSR-
GYASW The fourteenth sequence is designated 34–183RVE.T7 or SEQ.ID.NO:27.

TATCGGTGTCGAACTCGTGCGACAGGC-
CGTCGATCGCGACGCTGACGATC GTGGTGTCCAG-
CATCGACGCGATCGCGCCGATCACCAG-
GATCACGCCCA
GTCGGATGAGTGCGGGGTCCAGCCG-
GTCGGATGCGGATTGCTCGGGGGC GGAA-
GAAGGGGCCCCCGTGGACGGGCTAGT-
CATGCGAGGGACTCTACAC
CGTGTGGTGTAGTTGCTGTATCCTCCT-
GTTCTGTGGTTACCAATGCACGGA CTTCCGCCGT-
TGTCGGCGCGCACTCCCGC-
CGACTCGCGCACTCCCGCC
GGCGCCGGCAAGCGGCTGCGC-
CAGGGGTCCCCGAAGAAGCGCGCGGCG ATCG-
CACGGGCGGCGTTCGAGCTGTTCGTGGC-
CCAAGGCGTCGCCGGCA
CCAGCGTCGATGCCATCGCCGC-
CGAAGCGGGCGTCTCCAGCGCACCGTC TACGAC-
TACTACGGCAGCAGGAGCGGCTCTC-
CTCTCCGTCATCGAGACGC
GAGCGCGTACGCGACAGTCGCGGA-
CATCTGGACGCACCTCGCGAGTCGA CGGCACGAT-
GCATCGCGCACGACGACTCAGCGGG

The fifteenth sequence is designated 34–183R1A.2 or SEQ.ID.NO:28.

ATCCCGAAGAACTCCGCGTCGAAGTCTC-
CGGCGCCGTTCACGAAGCCGC CCTCGCGGACG-
TACGAGGTACCGGGGTGGTCGGGGTC-
CGGGTGGTACAG
GGCGTCCATGTCCAGCCCCGGTCG-
GTGGGGAACGCGGTCATCCCGTCA CGGCCCTCG-
GCCACCAGCCGCCACAGGTCTTCGGGC-
GACTCCACATCGC
CCGGGAGGCGGCAGGCCATCGCCAC-
GATCGCGATGGGGTCATCATCGGC GACGGCCAC-
CGCCGTGGCCTCGGTGACGTCCTCCG-
CACCGAGCAACTCG
GCGCGCAGGTGCTGGGCCAGCGCGTTCG-
GCGAGGGGTGGTCGAAGACGA GGGTG-
GCGGGCAGCCGCAGCCCGGTGGCGGCGT-
TCAGCCGGTTGCGGAG
TTCCACGGCCGTGAGCGAGTCGAAGC-
CAGCTCCTTGAACGCCTTCGTCGC GTTCACGGCT-
TCCTGCGAGGTGTGCCGAGCACGGCG-
GCACGTCGGCGCG
TACAGGTCCAGCAGGATGCGCG-
GCTCGCTCGGACGCGGCGGCAGCGGCG
TGCAGCGCGAGCCCGGCGCCGTGCGTAC-
GACGCGCGACGCGCGGACGTG GCGTACAGCCCT-
GAACGCGCGGAGCCACCGTCTGCGACGC-
CGGCAGTCA
GTGAGGGACCGACCGTGTTCGGCAGC-
CGCTGACGGTCAACGTCATCAAT GCATGTGGA-
CATCGCCGCTATCGGCGATTCGCT-
TCAAGTCGGATCAGTAC TCGTCAGGCAGAAGAG

The sixteenth sequence is designated 34–122.2.T7 or SEQ.ID.NO:29.

GCGGCCGCATAATACGACTCACTATAGG-
GATCTTCTTCCCGGCCAGCAAC ATGCCCAGTC-
CGAGGGCGAGTTTCGCCTTCTTCGT-
GCGCCCAAGGAGATA
GCCTCCCGTGATCGCGACCGCGATCT-
TGCCGTITGTCATCATCAATTCGCT CCCGAAGTC-
GAACGCGGCTTCGATGTGGACGGCCGGG-
TACCCACATACG
GAAAAGCCCCACTCGTCAAAAGAC-
GAGTGGGGCTTTTGTGCTCCGGGGA GCGTCAGGT-
CACTTGACGATCTTGGTGACCTGGCCG-
GCGCCGACGGTCCG
GCCACCCTCACGGATGGCGAACTTCAG-
GCCCTCCTCCATGGCGACCGGCT GGATCAGCTG-
GACGGACATCTCGGTGTTGTCGCCCG-
GCATGACCATCTCG
GTGCCCTCGGGGAGGGTCACAACGC-
CCGTCACGTCCGTGGTACGGAAGT AGAACTGCG-
GACGGTAGTGTTGAAGAACGGCGTGTG-
GCGGCCACCCTC
GTCCTGGACAGGATGTACGCCTGGCCTC-
GAACTCGGGTGTGCGGGGTGA CCGAGCCCGGCT-
GATGATGACCTGGCGCGCTCGACGTTCT-
CACGCTGATG
CGCGAGCAGCAGAACGACGTCTCAC-
CGGGCCTGCCCTCGTTCGAGCCAG CCTGCGGA-
CATTCCGATCCGGTGACGGTGGTC-
GAGGGTCTCTCCGGCTGA
TGCGATGATGTTGACGTTTCGTTGACCT-
CAGCACGCCGGACTGATCGCGG GTGACAACGATC-
CGACGGTATGGTAAACGTTCGTAATCGG

The seventeenth sequence is designated 34–123.3 or SEQ.ID.NO:30.

CCTCTCCGCACCCGTCCCTCCCCTCAC-
CTCATCTCGTGGCCCCGGCTCGCC TAAGTCGC-
CCCTGGCCGCCCGCCTCCCCTTTGC-
CTCTCCCTCTCTCTGGCG
GGTGGGGGGGGGGGGGTTC-
CCCCCTTTTTGCCTTGCCCCACCTCCGTGGG GGCT-
TGGGGAAATTGTTTTTTTTTCCATGCACT-
CAGTTATAGGGCCAGAAAT
TGGGTCACTGGGCCCCCCCATCGGAGGT-
CAGAGTGTATCGATAAGCTTGA ATATCCAGGC-
CCGACCAACTATCTCTTGGGT-
TGGGCAGCCGGTTGACTTC
ACGTGGCAGACGGCAGGGCCGATTGT-
TGTrCGCGCATCACCGTTGGAGG AGCAGGGCTA-
CATCTTCGTCAATCGCGGCGGTCTTGGC-
CGGGCTTGGACA
CCCTTGGCGGAACCGGTCCACATCGGCG-
GAAAGCTTGCCGGAGGTCGCC TAACGACAC-
GATCGCCCTCGCCGATTATTGAACGC-
CGACGGCAAGACCG
ACATCATCGGCCGGCAGGGCGGCACCAG-
CAAGATCGACATCATTCCCTT CGCGGGCGAGGTC-
GACGGCACCAACAGCTTCAACGCGC-
CCGAGCGGCTG
GGCCACCCTCCGGCGCAGACGTGACAT-
TCCCCCTGGGGCGCCGCCGACA TTCACCGGCTTC-
CGTGCCGTGCCCGAGCTTGCTICGTC-
CTGGCAACGACA
ACGTGCGAACCTTCGCCCAGTCCCAAC-
CCTTCCCTrCACCGTGAAACCAT GTGGCACGTG-
GAACCGCACGAACGTGTGTGAAGCAC-
CTGGGTGGTGGCA
GAAATGTCAGAACTGGTGCAACAACCGAATCA

The eighteenth sequence is designated 34–183.RVD.T3 or SEQ.ID.NO:31.

GATATCGGCGCCGATCTTCACGGGT-
TCACCATACGTCTTCAATCCATTGA GCGCACCG-
GAACCCGGATAGACAAATAATTCACTGC-
CATGCCGGACGAG
AATATCCTGCTTGCCGTCGCCGTCGAAC-
GAACCGGAATGACCGGTATAG GTCAGCAT-
TGACTCTCCCCGCTCCAGGGTTC-
GATAAGCGCCCCGCAAAG
GAATTACCGAGGAGCGCGCCGCCAG-
CATTTAGCCATCCTACGGACGCTA TTCATCCGG-
TAAACCCCTAGACCAACCCCTAGGGCTC-
CAGATGATGAGA
CACCACGTGTTGACAGCGGCCGC-
CCCGGGCTCCAACCTGATGACGTCAC CGCAGGT-
CAGCACGGATTCCCCAGGAAAC-
CCCAGCCAGCTCCGCGGCG
GTCGGCGACCGCTCCGGTGCGGCGGGC-
CGACCGGATGAATGCCCACTTC AGGCCCGCGGT-
GCGATGAACGTCACGTTTTCCGTACGA-
CATGTCCGCGCC

GTCCGGAAATAATGTGAGATGGCGGCA-
CATACTGCCACCCATTAGTATG GATCAGTAG-
GCGCTCTTTTTCGCTGACGTTCTGTGA-
CAGCCCACACCATC
GAGAGCGGCGCAGACAGTGCATCGCG-
CATGCATTCGCGCACGACGAGA CTCCACGAGGG-
GATTGTGGAGCTGGCGACGGATGAC-
CGAACTCACTCGG
CTACGATCATGCGGTCGACCTGCATGGT

The above sequence information can be used to generate nucleic acids of the invention as well as to generate additional sequence information regarding the PKS enzyme and modification enzymes of the invention.

The invention having now been described by way of written description and example, those of skill in the art will recognize that the invention can be practiced in a variety of embodiments, that the foregoing description and example is for purposes of illustration and not limitation of the following claims.

What is claimed is:

1. An isolated nucleic acid that comprises a coding sequence for a polyketide synthase enzyme identical to or isolated from a polyketide synthase enzyme coding sequence contained within a cosmid selected from the group consisting of cosmids 34–183, 34–122, and 34–126.

2. The isolated nucleic acid of claim 1 that is a recombinant expression vector.

3. The isolated nucleic acid of claim 1 that is cosmid 34–183.

4. The isolated nucleic acid of claim 1 that is cosmid 34–122.

5. The isolated nucleic acid of claim 1 that is cosmid 34–126.

* * * * *